US011801260B2

(12) United States Patent
Park et al.

(10) Patent No.: US 11,801,260 B2
(45) Date of Patent: *Oct. 31, 2023

(54) COMPOSITIONS FOR TREATING JOINT OR CONNECTIVE TISSUE DISEASE COMPRISING DEXTRAN OR POLOXAMER

(71) Applicant: MEDICINE PARK CO., LTD, Seoul (KR)

(72) Inventors: Yoo Sin Park, Seoul (KR); Il Hoon Lee, Seoul (KR)

(73) Assignee: MEDICINE PARK CO., LTD, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/669,840

(22) Filed: Feb. 11, 2022

(65) Prior Publication Data

US 2022/0233581 A1 Jul. 28, 2022

Related U.S. Application Data

(63) Continuation of application No. 16/769,808, filed as application No. PCT/KR2018/015244 on Dec. 4, 2018, now Pat. No. 11,278,565.

(30) Foreign Application Priority Data

Dec. 4, 2017 (KR) .................. 10-2017-0165271

(51) Int. Cl.
 *A61K 31/765* (2006.01)
 *A61P 19/02* (2006.01)
 *A61K 31/721* (2006.01)

(52) U.S. Cl.
 CPC .......... *A61K 31/765* (2013.01); *A61K 31/721* (2013.01); *A61P 19/02* (2018.01)

(58) Field of Classification Search
 CPC .................................................. A61K 31/765
 See application file for complete search history.

(56) References Cited

U.S. PATENT DOCUMENTS 5,902,800 A 5/1999 Green et al.
2005/0118230 A1 6/2005 Hill et al.
(Continued)

FOREIGN PATENT DOCUMENTS

JP 2002-509890 A 4/2002
KR 2007-0113572 A 11/2007
(Continued)

OTHER PUBLICATIONS

International Search Report and Written Opinion for Application No. PCT/KR2018/015244, dated Mar. 8, 2019.
(Continued)

*Primary Examiner* — Benjamin J Packard
(74) *Attorney, Agent, or Firm* — MARSHALL, GERSTEIN & BORUN LLP

(57) ABSTRACT

Disclosed is a composition for treating a joint disease or a connective tissue disease, a composition for cartilage regeneration, or a composition for treating an inflammatory disease, each of the compositions containing dextran, poloxamer or a mixture thereof. The composition stays in the joint or connective tissue for a long time due to the shock-absorbing effect, coating effect or anti-inflammation effect, relieves the shock, covers a damaged portion in a specific manner thereto, or reduces inflammation of an adhered portion. Thus, the composition may be useful for the treatment of the joint disease, the connective tissue disease, or for the cartilage regeneration.

12 Claims, 9 Drawing Sheets

Specification includes a Sequence Listing.

(56) References Cited

U.S. PATENT DOCUMENTS

2007/0237740 A1   10/2007   Reddington et al.
2015/0159151 A1   6/2015   Bright et al.

FOREIGN PATENT DOCUMENTS

WO   WO88/07060   *   9/1988   ............ C08B 37/02
WO   WO-2011/160146 A1   12/2011

OTHER PUBLICATIONS

Teixeira et al., "Self-Attaching and Cell-Attracting In-situ Forming Dextran-Tyramine Conjugates Hydrogels for Arthroscopic Cartilage Repair," Biomaterials, 33:3164-3174 (2012).
Hocking et al., "Dextran sulfate inhibits PMN-dependent hydrostatic pulmonary edema induced by tumor necrosis factor", Journal of Applied Physiology Respiratory, Environmental and Exercise Physiology, 70(3)1121-8, 1991.
Hocking et al., "Dextran sulfate and heparin sulfate inhibit platelet-activating factor-induced pulmonary edema", Journal of Applied Physiology, 72(1) 179-185, 1992.
Lu et al., "Dextran Sulfate Protects Pancreatic β-Cells, Reduces Autoimmunity, and Ameliorates Type 1 Diabetes", Diabetes 69, 1692-1707, 2020.
Pachekrepapol, "Effect of dextran and dextran sulfate on the structural and rheological properties of model acid milk gels", J. Dairy Sci. 9:2843-2852, 2015.

* cited by examiner

SEQUENCE LISTING

```
<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: MMP-3 forward primer

<400> SEQUENCE: 1
tgggaagcca gtggaaatg                                                    19

<210> SEQ ID NO 2
<211> LENGTH: 21
<212> TYPE: DNA
<213> ORGANISM: Artificial Sequence
<220> FEATURE:
<223> OTHER INFORMATION: MMP-3 reverse primer

<400> SEQUENCE: 2
ccatgcaatg ggtaggatga g                                                 21
```

```
<210> SEQ ID NO 3
<211> LENGTH: 20
<212> TYPE: DNA
<213> ORGANISM: Artificial Sequence
<220> FEATURE:
<223> OTHER INFORMATION: MMP-13 forward primer

<400> SEQUENCE: 3
ctgacctggg atttccaaaa                                              20

<210> SEQ ID NO 4
<211> LENGTH: 20
<212> TYPE: DNA
<213> ORGANISM: Artificial Sequence
<220> FEATURE:
<223> OTHER INFORMATION: MMP-13 reverse primer

<400> SEQUENCE: 4
acacgtggtt ccctgagaag                                              20

<210> SEQ ID NO 5
<211> LENGTH: 26
<212> TYPE: DNA
<213> ORGANISM: Artificial Sequence
<220> FEATURE:
<223> OTHER INFORMATION: GAPDH forward primer

<400> SEQUENCE: 5
ctcaactaca tggtctacat gttcca                                       26

<210> SEQ ID NO 6
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 6
cttcccattc tcagccttga ct                                           22

<210> SEQ ID NO 7
<211> LENGTH: 20
<212> TYPE: DNA
<213> ORGANISM: Artificial Sequence
<220> FEATURE:
<223> OTHER INFORMATION: IL-6 forward primer

<400> SEQUENCE: 7
tgatggatgc ttccaaactg                                              20

<210> SEQ ID NO 8
<211> LENGTH: 20
<212> TYPE: DNA
<213> ORGANISM: Artificial Sequence
<220> FEATURE:
<223> OTHER INFORMATION: IL-6 reverse primer

<400> SEQUENCE: 8
gagcattgga agttggggta                                              20

<210> SEQ ID NO 9
<211> LENGTH: 21
<212> TYPE: DNA
<213> ORGANISM: Artificial Sequence
<220> FEATURE:
<223> OTHER INFORMATION: IL-10 forward primer
```

```
<400> SEQUENCE: 9
gttgccaagc cttgtcagaa a                                              21

<210> SEQ ID NO 10
<211> LENGTH: 20
<212> TYPE: DNA
<213> ORGANISM: Artificial Sequence
<220> FEATURE:
<223> OTHER INFORMATION: IL-10 reverse primer

<400> SEQUENCE: 10
tttctgggcc atggttctct                                                20
```

COMPOSITIONS FOR TREATING JOINT OR CONNECTIVE TISSUE DISEASE COMPRISING DEXTRAN OR POLOXAMER

CROSS-REFERENCE TO RELATED APPLICATIONS

This application is a continuation of U.S. application Ser. No. 16/769,808, filed Jun. 4, 2020, which is a U.S. National Phase of International Application No. PCT/KR18/15244, filed Dec. 2, 2018, which claims priority to Korean Application No. 10-2017-0165271, filed Dec. 4, 2017, the disclosures of which are incorporated herein by reference.

INCORPORATION BY REFERENCE OF MATERIALS SUBMITTED ELECTRONICALLY

This application contains, as a separate part of the disclosure, a Sequence Listing in computer readable form (Filename: 55696A_Seqlisting; Size: 2,271 bytes; Created: Feb. 11, 2022), which is incorporated by reference in its entirety.

TECHNICAL FIELD

The present disclosure relates to a composition for treating a joint disease or a connective tissue disease, a composition for cartilage regeneration, or a composition for treating an inflammatory disease, each of the compositions containing dextran, poloxamer or a mixture thereof.

BACKGROUND ART

A joint is a portion where bones joint each other, and is composed of a cartilage, an articular capsule, a synovial membrane, a ligament, a tendon, and a muscle so that a joint motion between the bones is smooth. The joint serves to absorb a shock generated by movement. Arthritis means that the joint has an abnormal function due to inflammation due to various causes. A connective tissue joins tissues with each other in an animal to form an organ. The connective tissue may include, for example, cartilages, intervertebral discs, tendons, ligaments, bones, skins, fat tissues, blood vessels, and intestinal tissues.

Drugs used to treat the arthritis may be classified based on a main mechanism of action such as reducing inflammation, delaying disease progression, and reducing a concentration of a metabolic products such as uric acid. Many arthritis treatment drugs reduce inflammation. Inflammation is a pathological process that causes pain, swelling, fever, redness, and stiffness. Drugs that quickly relieve the inflammation include nonsteroidal anti-inflammation agents, including aspirin, and steroidal anti-inflammation agents, including cortisone. However, these anti-inflammatory and anti-inflammation agents, etc., mainly relieve a pain rather than treat the disease. Many complications occur when taking the anti-inflammatory and anti-inflammation agents for a long time. In particular, the steroidal anti-inflammation agent may be irrelevant to treatment of a cause of the disease and may have a temporary reduction of the pain due to the temporary anti-inflammation action, thereby inducing overuse of the joint. This may destroy the joint and exacerbate a disability.

Therefore, a conventional treatment agent used for a joint damage such as arthritis may have limited effectiveness and may have obvious toxic side effects, and may not be used continuously for a long time. Thus, there is an urgent need for a new treatment method or a new treatment agent of the joint damage that overcomes the shortcomings of the conventional treatment method.

Meanwhile, dextran refers to a polymer of D-glucose as a polysaccharide and has a structure similar to starch or glycogen. In the dextran, D-glucose forms a straight chain shape via $\alpha$-1,6 bonds, and $\alpha$-1,4 or $\alpha$-1,3 bonds are branched therefrom in some sites. Commonly used high molecular weight dextran is known to cause allergic reactions frequently in a body. Dextran has been used as a blood extender, anticoagulant (anti-adhesion agent), and the like. Cross-linked dextran is used for a filler. However, it has not been reported that dextran is used as a treatment agent for a joint disease or a connective tissue disease. Poloxamer refers to a nonionic surfactant, and is known to be used as an emulsifier, stabilizer, and dissolution-aiding agent in addition to the surfactant.

Currently, a new treatment method or a new treatment agent is needed due to the limited effectiveness, the obvious toxic side effects, and the lack of persistence of the effect of the conventional treatment method for the joint disease or the connective tissue disease. There are no known studies on the treatment of the joint disease or the connective tissue disease using dextran or poloxamer, especially low molecular weight dextran or poloxamer which does not cause an allergic reaction when being administered into a body.

DISCLOSURE

Technical Problem

Thus, the present inventors have conducted studies for the treatment of the joint or connective tissue disease. From the studies, we have identified that dextran, poloxamer, or a mixture thereof does not cause allergic reactions and protects the joint and the connective tissue using a shock-absorbing effect, a coating effect, or an anti-inflammation effect on damaged portions of the joints and the connective tissues. In this way, the present disclosure has been completed.

A purpose of the present disclosure is to provide a pharmaceutical composition for treating a joint disease or a connective tissue disease, a composition for cartilage regeneration, or a pharmaceutical composition for treating an inflammatory disease, each of compositions containing dextran, poloxamer or a mixture thereof.

Technical Solution

To achieve the purpose, the present disclosure provides a pharmaceutical composition for treating a joint disease or a connective tissue disease, the composition containing dextran, poloxamer or a mixture thereof.

Further, the present disclosure provides a pharmaceutical composition for preventing or treating a joint disease or a connective tissue disease, the composition containing a mixture of two kinds selected from the group consisting of dextran 1, dextran 5 and poloxamer 188.

Further, the present disclosure provides a pharmaceutical composition for preventing or treating an inflammatory disease, the composition containing dextran, poloxamer or a mixture thereof as an effective ingredient.

Further, the present disclosure provides a composition for cartilage regeneration, the composition containing dextran, poloxamer or a mixture thereof as an effective ingredient.

Further, the present disclosure provides a composition for cartilage regeneration, the composition containing a mixture of two kinds selected from the group consisting of dextran 1, dextran 5 and poloxamer 188.

Advantageous Effects

The composition according to the present disclosure stays in damaged portions of the joint or connective tissue for a long time due to the shock-absorbing effect, coating effect or anti-inflammation effect, relieves the shock, covers a damaged portion in a specific manner thereto, or reduces inflammation of an adhered portion.

Thus, the composition according to the present disclosure may be useful for the treatment of the joint disease, the connective tissue disease, or for the cartilage regeneration.

MODES OF THE INVENTION

Figure 1:
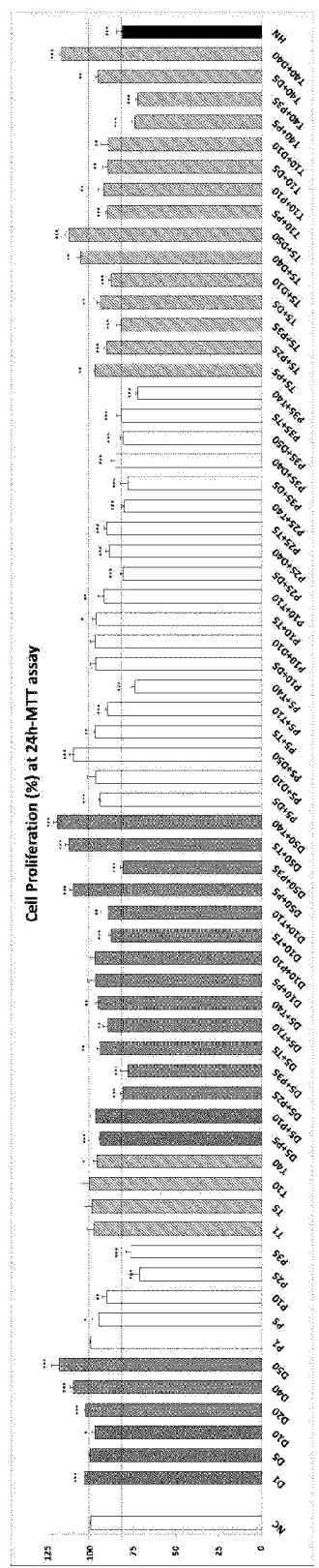
FIG. 1 is a diagram showing results of identifying a cell proliferation ability of chondrocyte in 24 hours after normal chondrocyte is treated with dextran, poloxamer, or a mixture thereof (*//* represent significance levels of $p<0.05$/$p<0.01$/$p<0.001$ respectively, compared to a negative control (nc)).

Hereinafter, the present disclosure will be described in detail.

The present disclosure provides a pharmaceutical composition for treating a joint disease or a connective tissue disease, the composition containing dextran, poloxamer or a mixture thereof. Further, the present disclosure provides a method of preventing or treating a joint disease or a connective tissue disease, the method including administering dextran, poloxamer or a mixture thereof to a subject in need thereof.

In the present disclosure, "dextran" refers to a polymer of D-glucose as one of polysaccharides. Dextran has a structure similar to starch or glycogen. In the dextran, D-glucose forms a straight chain shape via α-1,6 bonds, and α-1,4 or α-1,3 bonds are branched therefrom in some sites. Dextran may be used as a blood extender and anticoagulant. Depending on a purpose, a molecular weight of dextran may vary. According to the present disclosure, the dextran may have an average molecular weight of 500 to 10,000 Da. The molecular weight thereof may be preferably in a range of 500 to 8,000 Da, more preferably, in a range of 1,000 to 5,000 Da. Depending on the molecular weight, dextran has a name of 'dextran 1' for an average molecular weight of 1,000 Da, a name of 'dextran 5' for an average molecular weight of 5,000 Da, or a name of 'dextran 10' for an average molecular weight of 10,000 Da.

In general, it is known that when dextran of average 8,000 Da or greater is administered to a human body, a high risk of allergic reaction may occur. In particular, the allergic reaction may cause an anaphylaxis as a rapid systemic reaction caused by an antigen-antibody immune response, which may be quite dangerous. However, use of low average molecular weight dextran, preferably, 1,000 Da to 5,000 Da dextran according to the present disclosure has an advantage of minimizing the allergic reaction. The low average molecular weight dextran, preferably, 1,000 Da to 5,000 Da dextran according to the present disclosure has a slower rate of decomposition in the body, compared to a known substance (for example, hyaluronic acid). Thus, the use of low average molecular weight dextran, preferably, 1,000 Da to 5,000 Da dextran according to the present disclosure has an advantage that the therapeutic effect of the joint disease or the connective tissue disease may be maintained for a long time.

Further, according to the present disclosure, dextran of a low molecular weight may have no allergic reaction, and may have an early onset in action, and may spread over a wide range, compared to dextran of 8,000 Da or greater.

In a preferred example of the present disclosure, dextran 1 and dextran 5 are used. The dextran 1 and the dextran 5 may be used in combination with each other and may be used in combination with poloxamer 188.

In the present disclosure, two kinds selected from the group consisting of dextran 1, dextran 5 and poloxamer 188 may be mixed with each other in a volume ratio of 1:1.

As used herein, a concentration of the dextran may be expressed as a percentage of a mass (g) concentration (w/v) in 100 cc of a solvent. For example, when dextran 1 as a single effective ingredient is contained in the composition, the dextran 1 may be contained therein at a concentration of 2 to 40 (w/v) %. When dextran 5 as a single effective ingredient is contained in the composition, the dextran 5 may be contained therein at a concentration of 2 to 30 (w/v) %.

Further, when dextran is contained, as a mixture of the dextran 1 and the dextran 5, or a mixture of dextran and poloxamer, in the composition, the concentration of dextran may vary depending on the mixture configuration. For example, when the mixture of dextran 5 and dextran 1 is contained in the composition, the concentration of the dextran 5 may be in a range of 2 to 40 (w/v) %, while the concentration of the dextran 1 may be in a range of 2.5 to 40 (w/v) %; or the concentration of dextran 5 may be in a range of 4 to 40 (w/v) %, while the concentration of dextran 1 may be in a range of 5 to 40 (w/v) %.

When dextran is present at a high concentration in the composition, a disadvantage may occur that it is difficult to form a shape due to an excessive increase in viscosity due to the nature of polysaccharides in which polysaccharides contains moisture. For this reason, dextran has been conventionally used at a concentration of 5% or smaller. However, the dextran is contained in the composition according to the present disclosure at concentration of 2 to 40 (w/v) % depending on the molecular weight thereof. Thus, the therapeutic effect of the joint disease or connective tissue disease may be maximized when using the composition according to the present disclosure. To increase or stabilize the solubility of dextran, the composition according to the present disclosure may additionally contain an additive. The additive may include sugar alcohols, monosaccharides, or divalent cations including $CaCl_2$.

In the present disclosure, "poloxamer" refers to a nonionic triblock copolymer composed of a central hydrophobic chain of polyoxypropylene (poly(propylene oxide)) flanked by two hydrophilic chains of polyoxyethylene (poly(ethylene oxide)). The poloxamer has temperature sensitivity, and thus converts to between sol and gel according to a concentration and a temperature. The properties of poloxamer vary depending on a ratio between contents of polyoxypropylene and polyoxyethylene. The poloxamer is used as an emulsifier, stabilizer, and a dissolution aiding agent in addition to surfactant.

In accordance with the present disclosure, the poloxamer may have an average molecular weight of 100 to 20,000 Da.

The poloxamer may be selected from the group consisting of poloxamer 101, poloxamer 105, poloxamer 105 benzoate, poloxamer 108, poloxamer 122, poloxamer 123, poloxamer 124, poloxamer 181, poloxamer 182, poloxamer 182 dibenzoate, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and poloxamer 407. The poloxamer may preferably include poloxamer 188, but is not limited thereto.

As used herein, the concentration of the poloxamer is expressed as a percentage of a mass (g) concentration (w/v) in 100 cc of a solvent. The poloxamer may be contained in the composition at a concentration of 1 to 50 (w/v) % and a concentration of 2 to 30 (w/v) %. For example, poloxamer 188 may be contained in the composition at a concentration of 1 to 15 (w/v) % or 1 to 10 (w/v) % when the poloxamer 188 is contained as a sole effective ingredient in the composition.

In order to increase or stabilize the solubility of the poloxamer, the composition according to the present disclosure may further contain an additive such as sugar alcohols, monosaccharides, and divalent cations. Alternatively, sterile or physiological saline may be contained in the composition without additional additives.

According to the present disclosure, the pharmaceutical composition may contain a mixture of dextran and poloxamer. Especially when poloxamer 188 is mixed with dextran, the poloxamer 188 may be used in combination with dextran 1 or dextran 5. For example, when poloxamer 188 is mixed with dextran 5, the concentration of the dextran 5 may be in a range of 2 to 40 (w/v) %, while the concentration of the poloxamer 188 may be in a range of 1 to 20 (w/v) %. Alternatively, the concentration of dextran 5 may be in a range of 4 to 40 (w/v) %, and the concentration of poloxamer 188 may be in a range of 2 to 10 (w/v) %.

Further, for example, when poloxamer 188 is mixed with dextran 1, the concentration of the dextran 1 may be in a range of 2.5 to 40 (w/v) %, while the concentration of the poloxamer may be in a range of 1 to 5 (w/v) %. Alternatively, the concentration of dextran 1 may be in a range of 45 to 55 (w/v) %, while the concentration of poloxamer 188 may be in a range of 1 to 2 (w/v) %.

Poloxamer 188 may exhibit toxicity when the poloxamer 188 is contained in the composition at a concentration in excess of 25 (w/v) %, that is, at a high concentration. Thus, when poloxamer 188 is mixed with dextran, the concentration thereof may be adjusted appropriately.

In one embodiment, dextran:poloxamer may be contained in the pharmaceutical composition according to the present disclosure, for example, at a following (w/v) % ratio: 5:0.05, 5:0.5, 5:5, 5:10, 5:20, 5:30, 5:40, 5:50, 5:100, 5:150, 5:200, 10:0.1. 10:1, 10:10, 10:20, 10:30, 10:40, 10:50, 10:100, 10:150, 10:300, 10:400, 50:0.5, 50:1, 50:5, 50:10, 50:20, 50:30, 50:40, and 50:50. For example, the ratio may be in a range of 1:0.01 to 1:40. When poloxamer 188 1 (w/v) % and dextran 1 40 (w/v) % may be mixed with each other, the ratio may be 1:40. When poloxamer 188 20 (w/v) % and dextran 5 2 (w/v) % are mixed with each other, the ratio may 1:0.1. Thus, the ratio may be in a range of 1:0.1 to 1:40. In this connection, an average molecular weight of the dextran may be in a range of 1,000 Da or 5,000 Da, while the poloxamer may include poloxamer 188 which has an average molecular weight of 8,500 Da. Further, in one embodiment of the present disclosure, when the composition contains a mixture of two kinds selected from the group consisting of dextran 1, dextran 5 and poloxamer 188, the mixed components may be contained in the composition in a volume ratio of 1:1.

Further, in one embodiment of the present disclosure, the pharmaceutical composition according to the present disclosure contains a mixture of dextran 1 and dextran 5. A ratio between contents of dextran 1 and dextran 5 in the pharmaceutical composition may include, for example, a following (w/v) % ratio: 5:0.05, 5:0.5, 5:5, 5:10, 5:20, 5:30, 5:40, 5:50, 5:100, 10:0.1. 10:1, 10:10, 10:20, 10:30, 10:40, 10:50, 10:100, 10:150, 10:200, 50:0.5, 50:1, 50:5, 50:10, 50:20, 50:30, 50:40, 50:50, 50:1,000. For example, the ratio may be in a range of 1:0.01 to 1:20. When mixing dextran 1 2.5 (w/v) % and dextran 5 40 (w/v) % in one example, the ratio may be 1:16. When mixing dextran 1 40 (w/v) % and dextran 5 2 (w/v) %, the ratio may be 1:0.05. Thus, the ratio may be in a range of 1:0.05 to 1:16.

When the composition according to the present disclosure contains a mixture of dextran and poloxamer, a hydrophobic component of poloxamer may enhance the solubility of dextran or a combination drug, and a hydrophilic component of poloxamer such as PEG (polyethylene glycol) may preserve cell membranes and prevent adhesion to preserve a tissue. However, poloxamer may be easily diluted by body fluids and may be easily absorbed by body fluids. For this reason, when poloxamer is mixed with dextran, this may increase the stability of poloxamer in the body. Therefore, a mixture of dextran and poloxamer has a longer viscosity maintaining time and may cover the damaged joints or connective tissue areas, compared with dextran alone or poloxamer alone. The mixture may prevent pathological adhesions of tissues to reduce the inflammatory level caused by friction, so that the supply of nutrient substances thereto becomes smooth and the regeneration of tissues is enhanced. This effect may result from the shock-absorbing effect (cushion effect) or coating effect or anti-inflammation effect of the mixture of the dextran and poloxamer.

In the present disclosure, the term "shock-absorbing effect (cushion effect)" means an effect that the composition acts as a cushion that may reduce friction in the administered area, such as a joint thereby to absorb the shock applied thereto. The term "coating effect" refers to an effect that the composition coats a stiff area, for example, a damaged cartilage tissue in a joint at high speed to allow a knee joint to move comfortably. These effects may reduce the inflammatory response of the damaged joint site.

Therefore, the composition according to the present disclosure which induces the shock-absorbing effect and the coating effect or the anti-inflammation effect may be suitable for regenerating or improving the damaged tissue, and thus may be effectively used in the treatment of the joint disease or connective tissue disease. The above-described effect of the composition according to the present disclosure may be similar to that of a stem cell therapy currently used for the treatment of the joint disease, and may be competitive with the stem cell treatment agent that requires high skill and cost.

Meanwhile, the pharmaceutical composition for the prevention or treatment of the joint disease or connective tissue disease according to the present disclosure, the composition containing dextran, poloxamer or a mixture thereof, may further contain stem cells in order to enhance the effect of preventing or treating the target joint disease or connective tissue disease. Stem cells that may be contained in the composition in accordance with the present disclosure may include embryonic stem cells or adult stem cells. The adult stem cells may include mesenchymal stem cells, human tissue-derived mesenchymal stromal cells, human tissue-derived mesenchymal stem cells, multipotent stem cells, or amniotic epithelial cells. The stem cells may include stem cells derived from umbilical cord, umbilical cord blood, bone marrow, fat (or adipose tissue cells), muscle, nerve, skin, amniotic membrane and placenta (or placental tissue cells), urine, etc., but may not be limited thereto. The stem cell may include a stem cell or a concentrate thereof, a stem cell culture solution or a concentrate thereof, a culture secretion of stem cells or a concentrate thereof, or a combination thereof. The dextran or poloxamer in the composition may serve to specifically transport the stem cells to the damaged lesions of joints or connective tissue. Further, the dextran or poloxamer in the composition may settle on the lesion area to which the stem cells are carried, thereby to enhance the induction of the regeneration of the damaged tissue.

As used herein, the term "prevention" refers to all actions that inhibit or delay the onset of the joint disease or connective tissue disease via administration of the composition.

As used herein, the term "treatment" refers to any act of reducing or beneficially altering the symptoms of the joint disease or connective tissue disease via administration of the composition.

The pharmaceutical composition according to the present disclosure may further contain pharmaceutically acceptable additives and may be formulated in a formulation of a unit dosage form suitable for administration into a patient's body using conventional methods in the pharmaceutical field. Further, the formulation may be produced by mixing the composition with a pharmaceutically acceptable carrier or medium, for example, sterile water, physiological saline, vegetable oil, emulsifier, suspension, surfactant, stabilizer, excipient, vehicle, preservative, or binder, etc. and forming the mixture in a pharmaceutically acceptable unit dosage form.

The pharmaceutical composition may be in a solution or powder form. When the pharmaceutical composition has a powder form, the composition may be dissolved in a solvent immediately before administration. However, the present disclosure is not limited thereto. The formulation may be prepared in the most appropriate way while considering various situations that may occur during preparation of the drug.

An administration method of the pharmaceutical composition is not particularly limited. The composition may be administered via a general route of administration. The administration method of the pharmaceutical composition may include oral administration, injection, and infusion.

In the oral administration, the composition together with a pharmaceutically acceptable carrier and excipient may be formulated into a preparation such as tablets, pills, capsules, gels, syrups. However, a solid agent such as a tablet or a powder consumes a large absorption time. Thus, in the oral administration, preferably, a liquid type formulation may be used. In that case, the liquid type formulation may further contain suitable additives, for example, salts such as sodium chloride, buffers, and chelating agents.

Further, the formulation may be administered using a target drug delivery system such as a liposome coated with a specific antibody targeting a joint or connective tissue. Liposome may be selectively settled on an affected tissue.

When the pharmaceutical composition according to the present disclosure is formulated into a formulation for topical administration, the formulation may contain a buffer, an isotonic agent, etc. and may be dissolved in sterile distilled water, and then may be directly injected into an articular cavity, a connective tissue, intravenously, subcutaneously, intradermally, intraarticularly, or into a muscle of a subject, or may be applied to a skin, or may be patched thereon.

The subject may be one selected from mammals including humans, dogs, cats, pigs, horses, cows, sheep, mice, and monkeys, and may be preferably humans.

As used herein, the term "intraarticularly" refers to an injection of the pharmaceutical composition according to the present disclosure into a transdermal of the joint.

As used herein, the term "topical administration" refers to an injection of the pharmaceutical composition according to the present disclosure into a transdermal of an inflamed joint portion or of a portion adjacent thereto. Therefore, the topical injection is directed to the epidermis, dermis, muscle or any deep organ.

A main advantage for the topical administration is that it selectively limits an analgesic effect on the injured area. In addition, the topical administration enables high local concentration levels with little or no systemic release.

The pharmaceutical composition may additionally contain stabilizers, lubricants, buffers, isotonic control agents, anesthetics or antibacterial agents.

Further, the pharmaceutical composition may further contain an anti-inflammatory agent widely used in the art. The anti-inflammatory agent may be a nonsteroidal agent, a steroidal agent, or a combination thereof. Non-limiting examples of the nonsteroidal anti-inflammatory agents may include oxicam, for example, piroxicam, isoxiccam, tenoxycam, sudoxicam; salicylates, such as aspirin, disalside, benolylate, trilysate, saphapurine, sorprine, diflunisal and fendosal; acetic acid derivatives such as diclofenac, fenclofenac, indomethacin, sulindac, tolmetin, isoxepac, furofenac, thiopinac, zidomethacin, acematacin, fentiazac, zomepirac, clindanac, oxepinac, felbinac and ketorolac; phenamates such as mefenamic acid, meclofenamic acid, flufenamic acid, niflumic acid and tolfenamic acid; propionic acid derivatives such as ibuprofen, naproxen, benoxaprofen, flurbiprofen, ketoprofen, fenoprofen, fenbufen, indoprofen, pyrprofen, carprofen, oxaprozin, pranoprofen, miroprofen, thioxaprofen, suprofen, alminoprofen and thiapropenic; pyrazoles such as phenylbutazone, oxyphenbutazone, febrazone, azapropazone and trimethazone. Extracts of these nonsteroidal anti-inflammatory agents may be used.

Non-limiting examples of the steroidal anti-inflammatory agents may include corticosteroids, such as hydrocortisone, hydroxy-triamcinolone, alpha-methyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluchlorolone acetonide, fludrocortisone, flumethasone pivalate, fluorosinolone acetonide, fluorocinonide, flucortin butyl ester, fluocortolone, fluprednidene (flupredniliden) acetate, fluland lenolone, halcinonide, hydrocortisone acetate, hydrocortisone butyrate, methylprodnisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrizone, amcinafel, amcinafide, betamethasone, and balance of ester thereof, chloroprednisone, chlorprednisone acetate, clocortelone, clecinolone, dichlorison, difluprednate, fluchloronid, flunisolide, fluorometallon, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone and extracts thereof.

The pharmaceutical composition according to the present disclosure may be administered in a pharmaceutically effective amount. The term "pharmaceutically effective amount" means an amount sufficient to treat the disease. The effective dose amount may be determined according to the factors including the severity of the disease, the patient's age, weight, health, sex, patient's sensitivity to the drug, the time of administration, the route of administration and release percentage, duration of treatment, a drug to be combined with the composition according to the present disclosure, a drug to be used at the same time as the composition according to the present disclosure, and other factors well known in the medical field. The dose amount of dextran, poloxamer, or a mixture thereof varies over a wide range and is determined based on an individual requirement of each specific case.

The pharmaceutical composition according to the present disclosure may be administered in combination with a known drug for the treatment of the joint disease or connective tissue disease, and may be administered simultaneously or sequentially with or to the known drug.

The pharmaceutical composition according to the present disclosure may be administered in a divided manner, for example, one or several times, at a preferred administration interval, for example, one-week interval.

According to the present disclosure, the pharmaceutical composition containing dextran, poloxamer or a mixture thereof may reduce long-lasting pain in subjects suffering from the joint disease or connective tissue disease. Using the pharmaceutical composition according to the present disclosure may enable the treatment and/or prevention of acute as well as chronic joint disease or connective tissue disease while avoiding major drug side effects and not using deep invasive schemes.

As used herein, the term "connective tissue" refers to a tissue that is widely distributed in animal tissues and serves to connect, protect, and charge cells and organs. The connective tissue may be classified into fibrous connective tissue, glial tissue, and reticulum tissue. However, the fibrous connective tissue accounts for most of the connective tissue. For example, the connective tissue according to the present disclosure may include cartilage, intervertebral discs, tendons, ligaments, bones, skin, blood vessels, and intestinal tissues without limitation.

In the present disclosure, causes of the "joint disease" or "connective tissue disease" may be broadly classified into traumatic, infectious, inflammatory and degenerative causes. The composition or treatment agent according to the present disclosure may be used for the joint disease and connective tissue disease due to all causes of damage to the joint. The joint disease for which the composition according to the present disclosure is expected to be used effectively preferably includes osteoarthritis, preferably, degenerative osteoarthritis resulting from repetitive frictional forces, ankylosing spondylitis, psoriasis arthritis, traumatic arthritis, rheumatoid arthritis, patellofemoral syndrome, chronic inflammation or arthrosis. Further, the connective tissue disease for which the composition according to the present disclosure is expected to be used effectively may include the connective tissue diseases occurring when cartilage, intervertebral discs, tendons, ligaments, bones, skin, blood vessels, and intestinal tissues undergo collagen or moisture loss due to degenerative changes due to physical damage or repeated friction. In particular, the composition according to the present disclosure promotes anti-inflammation effect and synthesis of collagen, and has the effect of increasing the production level of aggrecan. Based on these effects, the composition according to the present disclosure may be effectively used for the prevention or treatment of at least one kind connective tissue disease selected from the group consisting of connective tissue diseases especially related to the inflammation, preferably, inflammatory bone joint disease, inflammatory dermatitis, inflammatory eye disease, inflammatory myositis, inflammatory gastrointestinal disease, cartilage disease, vasculitis and sprain.

In accordance with the present disclosure, examples of the composition which effectively expresses the anti-inflammation effect without showing cytotoxicity, inhibits the expression of MMP-3 and MMP-13 genes as proteins that destroy the cartilage substrate, promotes the synthesis of the type II collagen by protecting the cartilage, and increasing the production level of aggrecan may be provided as follows.

In the present disclosure, the composition may contain two selected from the group consisting of dextran 1, dextran 5 and poloxamer 188 in a volume ratio of 1:1.

Further, the present disclosure relates to a pharmaceutical composition for preventing or treating a joint disease or a connective tissue disease, the composition containing a mixture of two selected from the group consisting of dextran 1, dextran 5 and poloxamer 188.

As the dextran, dextran 1 may be contained as a single effective ingredient in the composition. The concentration of dextran 1 may be in a range of 2 to 40 (w/v) %.

As the dextran, dextran 5 may be contained as a single effective ingredient in the composition. The concentration of dextran 5 may be in a range of 2 to 30 (w/v) %.

Further, the poloxamer may be contained as a single effective ingredient in the composition. The concentration of poloxamer may be in a range of 1 to 15 (w/v) %.

In one example, according to the present disclosure, the mixture may include a mixture of dextran 5 and poloxamer. The concentration of the dextran 5 may be in a range of 2 to 40 (w/v) %, and the concentration of the poloxamer may be in a range of 1 to 20 (w/v) %.

Further, the mixture may include a mixture of dextran 5 and dextran 1. The concentration of the dextran 5 may be in a range of 2 to 40 (w/v) %, and the concentration of the dextran 1 may be in a range of 2.5 to 40 (w/v) %.

Further, the mixture may include a mixture of dextran 1 and poloxamer. The concentration of the dextran 1 may be in a range of 2.5 to 40 (w/v) %, and the concentration of the poloxamer may be in a range of 1 to 5 (w/v) %.

Further, the mixture may include a mixture of dextran 1 and poloxamer. The concentration of the dextran 1 may be in a range of 45 to 55 (w/v) %, and the concentration of the poloxamer may be in a range of 1 to 2 (w/v) %.

Further, an example of the present disclosure relates to an anti-inflammation composition based on the action of anti-inflammation, a pharmaceutical composition for preventing or treating an inflammatory disease, and a method for preventing or treating an inflammatory disease using the same.

Accordingly, the present disclosure provides a pharmaceutical composition for preventing or treating an inflammatory disease, the composition containing dextran, poloxamer or a mixture thereof as an effective ingredient.

Further, the present disclosure provides a method for preventing or treating inflammatory diseases, the method including administering dextran, poloxamer or a mixture thereof to a subject in need thereof.

Accordingly, the present disclosure specifically provides a pharmaceutical composition for preventing or treating an inflammatory disease, the composition containing at least one kind selected from the group consisting of dextran 1, dextran 5 and poloxamer 188. Further, the present disclosure provides a method for preventing or treating inflammatory diseases, the method including administering at least one kind selected from the group consisting of dextran 1, dextran 5 and poloxamer 188 to a subject in need thereof.

In accordance with the present disclosure, the inflammatory disease may include, but may not be limited to, inflammatory skin disease, inflammatory eye disease, inflammatory bone joint disease, inflammatory muscle disease, or inflammatory gastrointestinal disease.

When a mixture of two kinds selected from the group consisting of the dextran 1, dextran 5 and poloxamer 188 is administered to the subject, the mixture may exhibit a remarkably excellent anti-inflammation effect, compared to a case when each of the dextran 1, dextran 5 and poloxamer 188 is administered to the subject individually. Specifically, when dextran 1, dextran 5 and poloxamer 188 are administered to the subject, dextran 1 2 to 40 (w/v) %, dextran 5 2 to 40 (w/v) %, and poloxamer 188 1 to 10 (w/v) % may achieve excellent anti-inflammation effect in all ranges. For example, in preferred embodiments, a mixture of dextran 1 5 (w/v) % and poloxamer 188 2 (w/v) to 10 (w/v) %, a mixture of dextran 1 5 (w/v) % and dextran 5 4 to 40 (w/v) %, a mixture of dextran 1 50 (w/v) % and poloxamer 188 2 to 10 (w/v) %, a mixture of dextran 1 50 (w/v) % and dextran 5 4 to 40 (w/v) %, a mixture of poloxamer 188 2 (w/v) % and dextran 1 5 to 50 (w/v) %, a mixture of poloxamer 188 2 (w/v) % and dextran 5 4 to 40 (w/v) %, a mixture of poloxamer 188 10 (w/v) % and dextran 1 5 to 50 (w/v) %, a mixture of poloxamer 188 10 (w/v) % and dextran 5 4 to 40 (w/v) %, a mixture of dextran 5 4 (w/v) % and dextran 1 5 to 50 (w/v) %, a mixture of dextran 5 40 (w/v) % and dextran 1 5 to 50 (w/v) %, and a mixture of dextran 1 to 40 (w/v) %, dextran 5 40 (w/v) % and poloxamer 188 2 to 10 (w/v) % may exhibit a remarkably excellent anti-inflammation effect to treat the inflammatory disease.

Therefore, the mixture according to the present disclosure may include a mixture of dextran 1 and poloxamer 188. The concentration of the dextran 1 may be in a range of 2 to 40 (w/v) %, and the concentration of the poloxamer 188 may be in a range of 1 to 10 (w/v) %.

Further, the mixture according to the present disclosure may include a mixture of dextran 1 and dextran 5. The concentration of the dextran 1 may be in a range of 2 to 40 (w/v) % and the concentration of the dextran 5 may be in a range of 2 to 40 (w/v) %.

Further, the mixture according to the present disclosure may include a mixture of dextran 5 and poloxamer 188. The concentration of the dextran 5 may be in a range of 2 to 40 (w/v) %, and the concentration of the poloxamer 188 may be in a range of 1 to 10 (w/v) %.

Another example of the present disclosure relates to a composition for cartilage regeneration based on a cartilage substrate regeneration effect, and a method for cartilage regeneration using the same.

Accordingly, the present disclosure provides a composition for cartilage regeneration, the composition containing dextran, poloxamer or a mixture thereof as an effective ingredient.

Further, the present disclosure provides a method for cartilage regeneration, the method including administering dextran, poloxamer or a mixture thereof to a subject in need of cartilage regeneration.

The present disclosure specifically provides a composition for cartilage regeneration, the composition containing at least one kind selected from the group consisting of dextran 1, dextran 5 and poloxamer 188. The present disclosure specifically provides a method for cartilage regeneration, the method including administering at least one kind selected from the group consisting of dextran 1, dextran 5, and poloxamer 188 to the subject. The at least one kind selected from the group consisting of dextran 1, dextran 5, and poloxamer 188 may induce the collagen production level increase and the aggrecan production level increase and may decrease the expression level of MMP-3 or MMP-13.

When one kind selected from the group consisting of the dextran 1, dextran 5 and poloxamer 188 is administered to the subject, the content of dextran 1 may be in a range of 2 to 40 (w/v) %, the content of poloxamer 188 may be in a range of 1 to 15 (w/v) %, and the content of dextran 5 may be in a range of 2 to 30 (w/v) %.

Further, when a mixture of at least two kinds selected from the group consisting of dextran 1, dextran 5 and poloxamer 188 are administered to the subject, a mixture of dextran 1 5 (w/v) % and poloxamer 188 2 (w/v) %, a mixture of dextran 1 5 (w/v) % and dextran 5 4 to 40 (w/v) %, a mixture of dextran 1 50 (w/v) % and poloxamer 188 2 (w/v) %, and a mixture of dextran 5 4 to 40 (w/v) % and poloxamer 188 2 to 10 (w/v) % may be used. Those mixtures may achieve an excellent cartilage regeneration effect by increasing the production level of collagen or aggrecan and by inhibiting the expression of MMP-3 or MMP-13.

Therefore, the mixture according to the present disclosure may include a mixture of dextran 1 and poloxamer 188. The concentration of the dextran 1 may be in a range of 5 to 40 (w/v) %, and the concentration of the poloxamer 188 may be 2 (w/v) %.

Further, the mixture according to the present disclosure may include a mixture of dextran 1 and dextran 5. The concentration of the dextran 1 may be in a range of 5 (w/v) %, and the concentration of the dextran 5 may be in a range of 4 to 40 (w/v) %.

Further, the mixture according to the present disclosure may include a mixture of dextran 5 and poloxamer 188. The concentration of the dextran 5 may be in a range of 4 to 40 (w/v) %, and the concentration of the poloxamer 188 may be in a range of 2 to 10 (w/v) %.

Further, the most suitable embodiment in which the anti-inflammation and cartilage regeneration effects may be simultaneously achieved, thereby preventing or treating the joint disease or the connective tissue disease may include, but may not be limited thereto, a case when the composition contains each of dextran 1, dextran 5 and poloxamer 188 alone, and a case when a mixture of dextran 1 2.5 (w/v) %, dextran 5 2 to 30 (w/v) %, and poloxamer 188 1 to 15 (w/v) % may be contained in the composition. When mixtures of at least two kinds selected from the group consisting of dextran 1, dextran 5 and poloxamer 188 are used, a mixture of dextran 1 5 (w/v) % and dextran 5 4 to 40 (w/v) %, and a mixture of dextran 5 4 to 40 (w/v) %, and preferably 2 to 10 (w/v) %, poloxamer 188 2 (w/v) % and dextran 1 5 to 40 (w/v) % may be used.

Terms not defined herein have meanings commonly used in the technical field to which the present disclosure belongs.

EXAMPLES

Materials and Methods

In the present disclosure, experiments were performed using dextran 1 (Dextran 1, EP grade, Pharmacosmos), dextran 5 (Dextran 5, pharmaceutical quality, Pharmacosmos), poloxamer 188 (Poloxamer 188, cell culture grade, Sigma-Aldrich). Further, for the induction of arthritis, rhIL-1α (recombinant human IL-1α, Lot No. 200-01A) was purchased from PEPROTECH and used. As a positive control substance, indomethacin (Sigma-Aldrich, Lot No. 53-86-1), and sodium hyaluronate (25 mg/2.5 mL, Aragan injection, Dongkwang Pharmaceutical, specialty drug) were used.

Example 1. Preparation of Dextran, Poloxamer or a Mixture Thereof and Preparation for Experiment 1.1 Isolation and Culture of Cells After separating a hind limb joint of a 3-week-old male SD rat in a sterile state, only a cartilage tissue constituting the joint was collected and single-celled to separate primary rat chondrocytes. When the primary cultured cells were stable, they were used for testing. In order to specify the stabilized chondrocyte, the RNA isolation was conducted and then the expression level of type II collagen or SOX9 gene as a chondrocyte marker was identified using Real time RT-PCR and used in the test.

1.2 Cell Culture Method

Cells isolated from 1.1 were cultured in an incubator set at temperature 37° C., humidity 95%, and $CO_2$ 5%. Culture room temperature and humidity were identified on an 8 hours basis. As a medium, minimum essential medium (MEM) medium supplemented with 10% fetal bovine serum, 2 mL L-glutamine, 50 U/mL penicillin, and 50 μg/mL streptomycin was used. Cells were separated with detached solution (0.25 (w/v) % trypsin, 0.53 mM EDTA solution (3 mL)) when the number of cells has increased by 90% or more during the culture period. The cells were separated using centrifugation at 125×g for 10 minutes and were used in the following experiments.

1.3 Composition and Preparation of Test Group

The test group may be composed of a normal control (NC), inflammation-induced control (PC) as an osteoarthritis-induced model via treatment of rhIL-1α 5 ng/mL, and a treated group to which the test substance (single substance or mixture) was administered to the osteoarthritis-induced model at a varying concentration. The positive control includes indomethacin (IM) or sodium hyaluronate (HN) treated group which was treated at a single concentration. The test group is shown in a following Table 1.

TABLE 1

| Group | Inflammation inducing | Test substance treatment | Number of chondrocytes (cells) |
|---|---|---|---|
| NC(Negative control) | — | — | $5 \times 10^5$ |
| PC(Inflammation-induced positive control) | rhIL-1α 5 ng/mL | — | $5 \times 10^5$ |
| Test substance | | Single substance-Dextran 1 (D) concentration 1~6 level or Mixture (D + P) concentration 1~5 level Mixture (D + T) concentration 1~4 level | $5 \times 10^5$ |

TABLE 1-continued

| Group | Inflammation inducing | Test substance treatment | Number of chondrocytes (cells) |
|---|---|---|---|
| Test substance | | Single substance-Dextran 5 (P) concentration 1~5 or Mixture (P + D) concentration 1~4 Mixture (P + T) concentration 1~4 | $5 \times 10^5$ |
| Test substance | | Single substance-Poloxamer 188 (P) concentration 1~4 or Mixture (P + D) concentration 1~4 Mixture (P + T) concentration 1~4 | $5 \times 10^5$ |
| Positive control | | Sodium hyaluronate (HN) 8.33 mg/ml or Indometacin (IM) 5 µM | $5 \times 10^5$ |

D = dextran 1, T = dextran 5, P = poloxamer 188, NC = normal control, PC = inflammation-inducing substance (rhIL-1α) administered group, HN = sodium hyaluronate, IM = indomethacin, D + P = mixture of dextran 1 and poloxamer 188, D + T = mixture of dextran 1 and dextran 5, P + T = mixture of poloxamer 188 and dextran 5.

The concentrations of the components used in the present disclosure were expressed according to a following notation: D10=10 (w/v) % dextran 1 solution, P10=10 (w/v) % poloxamer 188 solution, T10=10 (w/v) % dextran 5 solution.

The test substance used in the present disclosure was prepared using the following method: dextran 1 (D) was prepared as single substance in 1 to 50 (w/v) %, dextran 5 (T) was prepared as single substance in 1 to 40 (w/v) %, poloxamer 188 (P) was prepared as single substance in 1 to 35 (w/v) %, based on a maximum concentration dissolved in the cell culture solution. When preparing a mixture thereof, two types of single substances were mixed in a volume ratio of 1:1 (v:v).

Each of dextran 1, dextran 5 and poloxamer 188 was completely dissolved at the administration concentration (w/v) thereof into a complete media (a minimum essential medium (MEM) containing 10% fetal bovine serum, 2 mL L-glutamine, 50 U/mL penicillin, 50 µg/mL streptomycin, etc.) as the medium prepared for cell culture. To completely dissolve the test substance in the complete media and homogenize the test substance, we slowly stirred the medium with a sterile spatula, stick, magnetic bar, etc., or shook the medium several times for a short time enough to avoid foaming, at cool temperatures, or at cold temperatures especially for the poloxamer 188, thereby to dissolve the test substance until the medium is completely transparent without floats. After the test substance was completely dissolved, the medium was filtered through a 0.22 µm pore size syringe filter, sealed, and stored in a refrigerated manner.

More specifically, the preparation of the single substance was performed in the following manner.

Preparation of 5% Single Substance ('D5') of Dextran 1

When preparing a 5% test solution of dextran 1, dextran 1 was aliquoted by 5 g, completely dissolved in complete media, and adjusted to a total volume of 100 mL to prepare a D5 (w/v) % test solution. Then, the test substance dissolved at a concentration of 0.05 g/mL was filtered using a 0.22 µm pore size syringe filter and stored in a refrigerated manner, and used.

Preparation of Mixture ('D5+P10') of 5% of Dextran 1 and 10% of Poloxamer 188

D5 and P10 were prepared respectively, and were filtered by a 0.22 µm pore size syringe filter, stored in a refrigerator, and mixed with each other in a ratio of 1:1 (v:v). Then, the mixture was shaken at low speed to avoid foaming.

Comparative Example: Indomethacin Treated Group (IM) Preparation

Indomethacin was completely dissolved in DMSO at a concentration of 5 mM, diluted with complete media, filtered with a 0.22 µm pore size syringe filter, and adjusted to a last concentration of 5 µM when treating the cells therewith.

Comparative Example: Sodium Hyaluronate Treated Group (HN) Preparation

Aragan injection (in which sodium hyaluronate 25 mg/2.5 mL, the drug form, was contained in a disposable sterile syringe) was injected into complete media and was diluted to sodium hyaluronate 25 mg/3 mL (=sodium hyaluronate 8.33 mg/mL) and was used immediately.

1.4 Dosing Method Setting

A doubling time of primary-cultured chondrocyte isolated from the rat was about 24 hours. Thus, the test substance was administered thereto when proliferation and stabilization thereof were appropriate. After incubating the chondrocyte in a 48 well or 24 well plate, each test substance was administered thereto once. The test solution was administered thereto such that the concentration of each test substance was 20% (v/v) of the total culture volume at 1 hour before rhIL-1α treatment for induction of arthritis. In 24 hours after the rhIL-1α treatment, cultures were collected and assays were conducted. However, when identifying the toxicity or proliferation ability of the test substance against the chondrocyte, only the test substance was administered without the rhIL-1α treatment.

1.5 Statistical Analysis

All experimental results were compared with the normal control (NC) or inflammation-induced positive control (PC) using a student T-test at p<0.05 level to indicate the significance level.

Example 2. Cytotoxicity Analysis

Cytotoxicity analysis was performed by identifying whether the proliferation ability of the chondrocyte changes according to the test substance treatment. Evaluation of cell proliferation ability was performed on both untreated chondrocytes not treated with rhIL-1α and chondrocytes which had inflammation induced via treatment with rhIL-1α. The treatment of the rat chondrocytes with each test substance was conducted, and then the incubation thereof for 24 hours and 48 hours was conducted. Then, MTT analysis (Thiazolyl Blue Tetrazolium Blue; Sigma, M5655) was conducted. In the evaluation of the cell proliferation ability of the test substance in the arthritis in-vitro model induced by the inflammation-inducing substance rhIL-1α, each test substance was administered to rat chondrocyte at 1 hour before the rhIL-1α treatment and then the chondrocyte was cultured for 24 hours and 48 hours. Then, MTT analysis (Thiazolyl Blue Tetrazolium Blue; Sigma, M5655) was conducted. The results were shown in FIGS. 1 to 4.

As shown in FIG. 1, the cell proliferation ability of dextran 1, dextran 5, poloxamer 188, or a mixture thereof in rat knee joint chondrocytes that were free of the inflammation were observed for 24 hours. Thus, it was identified that most of dextran 1, dextran 5, poloxamer 188, and a mixture thereof helps the cell proliferation without exhibiting the toxicity to the cells. However, when the poloxamer 188 was administered alone, and the poloxamer 188 had a concentration of 25 (w/v) % (P25), or 35 (w/v) % (P35), and the cell was incubated for 24 hours, cell proliferation ability was lower than that in the sodium hyaluronate (HN) (control drug (commercial drug)) administered group. Thus, this case was not suitable for single administration. Further, when some of the mixtures were used, the cell proliferation ability decreased when the cell was cultured for 24 hours. Thus, we identified the possibility of inducing the cytotoxicity when the poloxamer 188 was used at high concentration. Further, the cell proliferation ability in the D50+P35, P5+T40, P25+ T40, and P35+T40 experimental groups among the mixture treated groups was lower than that in the sodium hyaluronate (HN) (control drug (commercial drug)) administered group.

Figure 2:
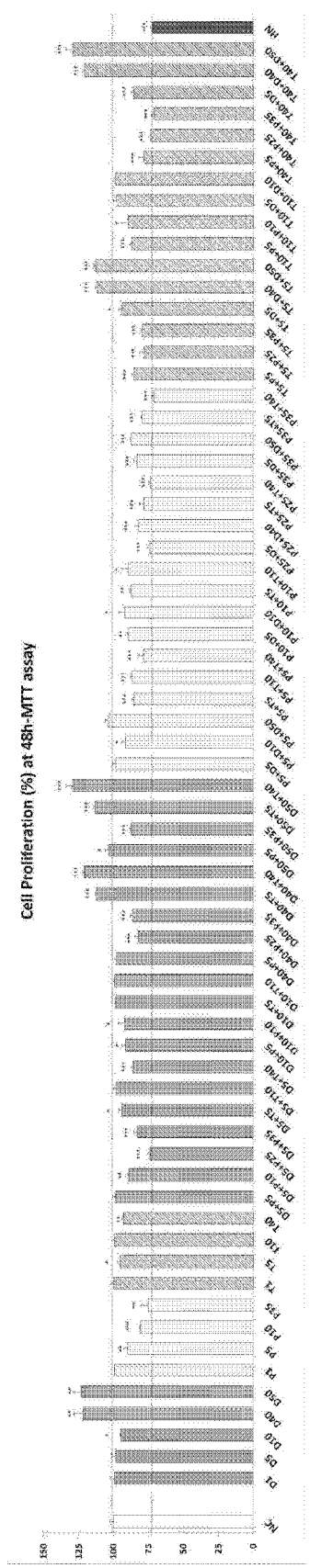
FIG. 2 is a diagram showing results of identifying a cell proliferation ability of chondrocyte in 48 hours after normal chondrocyte is treated with dextran, poloxamer, or a mixture thereof (*//* represent significance levels of $p<0.05$/$p<0.01$/$p<0.001$ respectively, compared to a negative control (nc)).

The cell proliferation ability of dextran, poloxamer, or a mixture thereof in rat knee joint chondrocytes that were free of inflammation were observed for 48 hours. As shown in FIG. 2, the results are similar to the results of 24-hour culture.

Based on these results, it was identified that when, in treatment of the normal knee joint chondrocyte, the concentration of dextran 1 (D) was increased to 50%, or the concentration of dextran 5 (T) was increased to 40%, chondrocyte proliferation was not inhibited, compared to the commercial drugs. The poloxamer 188 could be toxic to cartilage cells at a concentration of 25% or greater. Further, when the mixtures were used, the cell proliferation ability was improved compared to a case when the poloxamer 188 alone was used. It was identified that the poloxamer 188 is preferably mixed with dextran at a concentration of 10 (w/v) % or smaller in order not to induce the toxicity.

Figure 3:
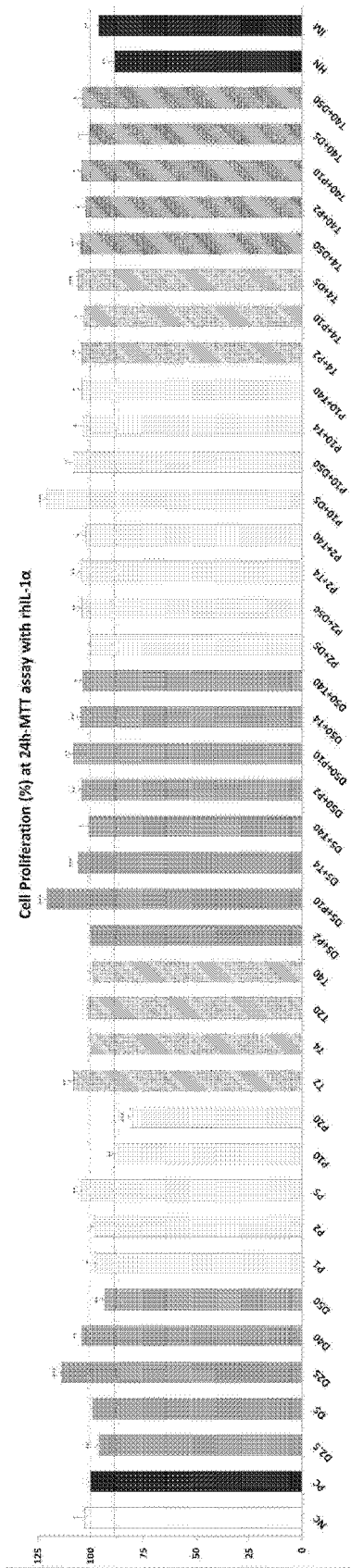
FIG. 3 is a diagram showing results of identifying a cell proliferation ability of chondrocytes in 24 hours after chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).
Figure 4:
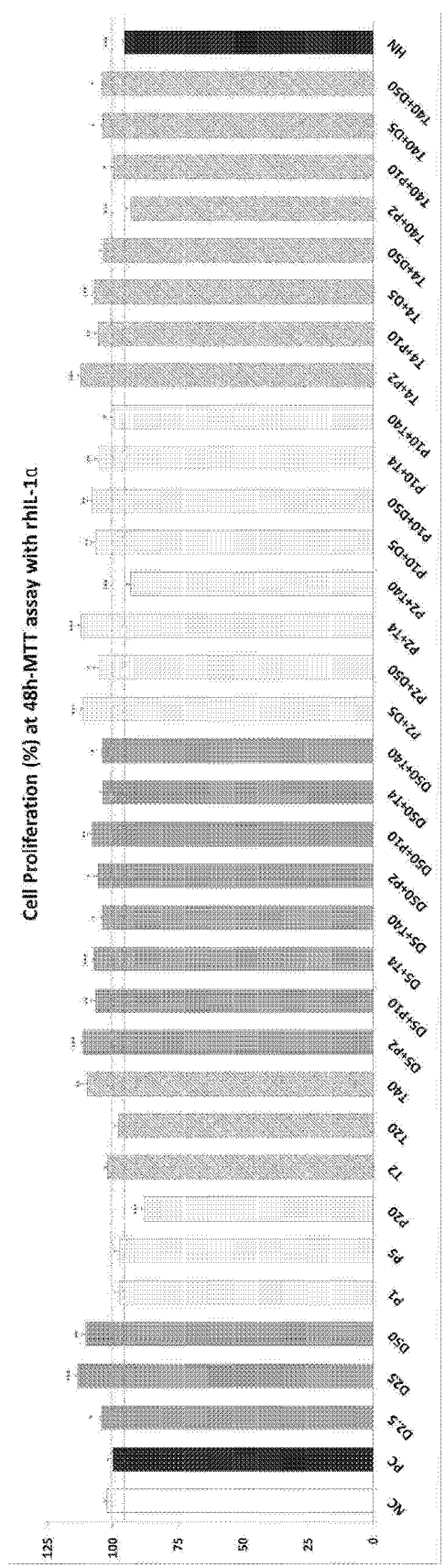
FIG. 4 is a diagram showing results of identifying a cell proliferation ability of chondrocytes in 48 hours after chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

In FIGS. 3 and 4, cell proliferation ability when the test substance was administered to the osteoarthritis in vitro model via the rhIL-1α treatment was observed for 24 hours and 48 hours, respectively.

As shown in FIG. 3, the poloxamer 188 inhibited the cell proliferation of the osteoarthritis model when the concentration thereof increased. However, it was shown that dextran 1 and dextran 5 did not inhibit the cell proliferation even at high concentrations. The poloxamer 188 exhibited the cell proliferation inhibition in the P10 single substance treated group. However, when the poloxamer 188 was used in combination with D5, D50, T4, T40, the cell proliferation increase effect was observed. Thus, it was identified that 1% to 10 (w/v) % of poloxamer 188 may be used when being mixed with the dextran.

In FIG. 4, 48-hour culture had the same results as those in the 24-hour culture. It was identified that the cell proliferation ability of the P10 treated group increased while P10 was mixed with dextran 1 or dextran 5.

Based on the above results, it was identified that dextran 1 and dextran 5 did not induce the cytotoxicity in normal cells and inflammation induced cells. On the other hand, poloxamer 188 was found to cause inhibition of the cell proliferation ability in both normal cells and inflammation induced cells when the poloxamer 188 was used as a single substance as the concentration thereof increased. It was identified that when the poloxamer 188 is mixed with dextran 1 or dextran 5 at the concentration of 1 to 10 (w/v) % of poloxamer 188, the poloxamer 188 was available without cytotoxicity.

Example 3. Identification of Anti-Inflammation Effect Based on Ratio Between Expression Levels of IL-10 and IL-6

An experiment was performed to identify the anti-inflammation effect of dextran 1, dextran 5 or poloxamer 188. Specifically, the concentration of dextran 1 was changed to 2.5 to 50 (w/v) %, that of dextran 5 was changed to 2 to 40 (w/v) %, and that of poloxamer 188 was changed to 1 to 20 (w/v) %. The single substance administration and the mixture administration were conducted. Thus, a ratio between expression levels of IL-10 and IL-6 was evaluated. To induce the inflammation, the inflammation-inducing substance rhIL-1α was administered to a target cell. When the ILIL-1α and the test substance (single substance, mixture thereof) were administered together, the ratio between expression levels of IL-10 and IL-6 was identified. As the ratio between expression levels of IL-10 and IL-6 increased, the anti-inflammation effect may be excellent.

The composition of the primer used in the experiment was shown in the following Table 2. GAPDH as a housekeeping gene was used as a control. The results are shown in Table 3A to Table 3B, and FIG. 5.

TABLE 2

|       | Forward direction | Reverse direction |
|-------|-------------------|-------------------|
| IL-6  | 5'- TGA TGG ATG CTT CCA AAC TG -3' | 5'- GAG CAT TGG AAG TTG GGG TA-3' |
| IL-10 | 5'- GTT GCC AAG CCT TGT CAG AAA -3' | 5'- TTT CTG GGC CAT GGT TCT CT -3' |
| GAPDH | 5'- CTC AAC TAC ATG GTC TAC ATG TTC CA -3' | 5'- CTT CCC ATT CTC AGC CTT GAC T -3' |

After mixing the primer, SyBr green (SYBR Premix Ex Taq, Takara, RR420A) and template with each other, Real time RT-PCR was executed thereon via a intercalating method using Real time RT-PCR (CFX 96 touch, Bio rad, Hercules, Calif., USA). The quantitative result (gene expression level) obtained by applying a Ct value to a calibration curve was converted to a value obtained by dividing the gene expression level by a quantitative result of GAPDH as a housekeeping gene.

administered group, a significant ratio increase was observed. This indicated that the anti-inflammation efficacy was excellent when administering the mixture.

Considering that in the 50 (w/v) % of dextran 1 administered group, the increase of the ratio between expression levels of IL-10 and IL-6 was significant, but the increase was not noticeable, the increase of the ratio between expression levels of IL-10 and IL-6, that is, preferably, the anti-inflammation effect in the osteoarthritis induced model was

TABLE 3A

| IL-10/IL6 Ratio | NC | PC | D2.5 | D5 | D25 | D40 | D50 | P1 | P2 | P5 |
|---|---|---|---|---|---|---|---|---|---|---|
| Mean/GAPDH | 0.403 | 0.546 | 0.563 | 0.489 | 0.511 | 0.524 | 0.596 | 1.258 | 0.781 | 1.506 |
| S.D | 0.032 | 0.005 | 0.031 | 0.034 | 0.027 | 0.013 | 0.027 | 0.119 | 0.018 | 0.087 |
| T-test vs. PC | 0.001 | | 0.202 | 0.023 | 0.045 | 0.026 | 0.017 | 0.000 | 0.000 | 0.000 |

| IL-10/IL6 Ratio | P10 | P20 | T2 | T4 | T20 | T40 | HN | IM |
|---|---|---|---|---|---|---|---|---|
| Mean/GAPDH | 0.862 | 0.651 | 1.278 | 0.722 | 0.789 | 0.474 | 9.245 | 1.484 |
| S.D | 0.070 | 0.040 | 0.044 | 0.034 | 0.056 | 0.003 | 0.826 | 0.035 |
| T-test vs. PC | 0.001 | 0.005 | 0.000 | 0.000 | 0.001 | 0.000 | 0.000 | 0.000 |

Ratio between gene expression levels of IL-10 and IL-6 due to administration of single substance of each of dextran 1 (D), dextran 5 (T), and poloxamer 188 (P) to chondrocyte treated with RhIL-1α for 24 h noticeable when administering the mixture of dextran 1 (D) with poloxamer 188 (P) or dextran 5 (T) rather than increasing the concentration of dextran 1 (D). In particular, the anti-inflammation effect was found to be remarkably supe-

TABLE 3B

| IL-10/IL-6 Ratio | NC | PC | D5 + P2 | D5 + P10 | D5 + T4 | D5 + T40 | D50 + P2 | D50 + P10 | D50 + T4 | D50 + T40 | P2 + D5 | P2 + D50 | P2 + T4 | P2 + T40 | P2 + D5 | P2 + D50 |
|---|---|---|---|---|---|---|---|---|---|---|---|---|---|---|---|---|
| Mean/GAPDH | 0.403 | 0.546 | 0.904 | 1.309 | 3.478 | 6.016 | 1.326 | 2.200 | 8.822 | 5.304 | 0.904 | 1.326 | 1.417 | 2.458 | 1.309 | 2.200 |
| S.D | 0.032 | 0.005 | 0.056 | 0.084 | 0.488 | 0.337 | 0.100 | 0.441 | 1.160 | 0.588 | 0.056 | 0.100 | 0.167 | 0.400 | 0.084 | 0.441 |
| T-test vs. PC | 0.001 | | 0.000 | 0.000 | 0.000 | 0.000 | 0.000 | 0.001 | 0.000 | 0.000 | 0.000 | 0.000 | 0.000 | 0.000 | 0.000 | 0.000 |

| IL-10/IL-6 Ratio | P10 + T4 | P10 + T40 | T4 + P2 | T4 + P10 | T4 + D5 | T4 + D50 | T40 + P2 | T40 + P10 | T40 + D5 | T40 + D50 | HN | IM |
|---|---|---|---|---|---|---|---|---|---|---|---|---|
| Mean/GAPDH | 1.373 | 8.094 | 1.417 | 1.373 | 3.478 | 8.822 | 2.458 | 8.094 | 6.016 | 5.304 | 9.245 | 1.484 |
| S.D | 0.016 | 0.114 | 0.167 | 0.160 | 0.488 | 1.160 | 0.040 | 0.114 | 0.337 | 0.588 | 0.826 | 0.035 |
| T-test vs. PC | 0.000 | 0.000 | 0.000 | 0.000 | 0.000 | 0.000 | 0.000 | 0.000 | 0.000 | 0.000 | 0.000 | 0.000 |

Figure 5:
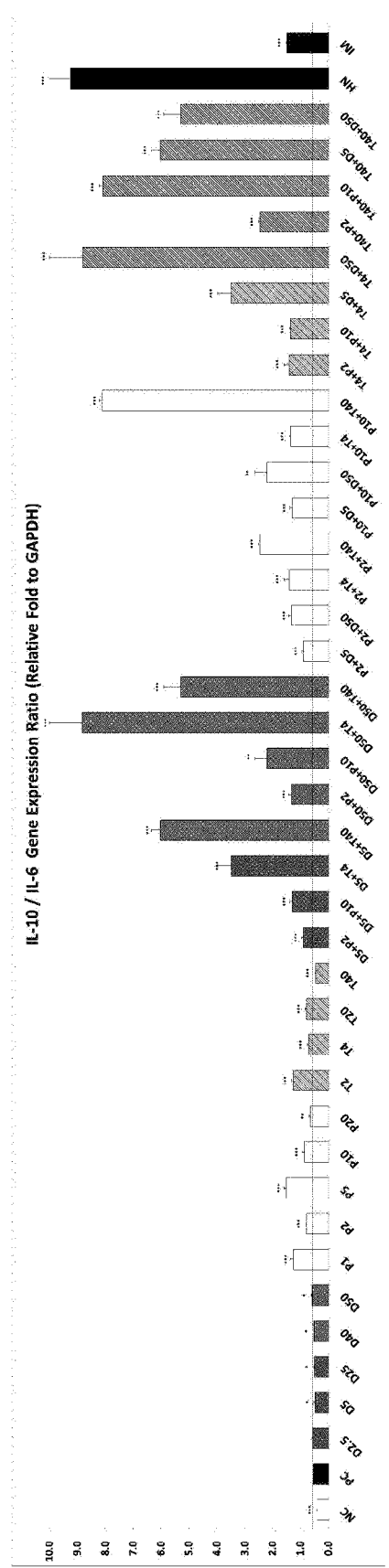
FIG. 5 is a diagram showing results of identifying a ratio between expression levels of IL-10 gene and IL-6 gene when chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

Ratio between gene expression levels of IL-10 and IL-6 due to administration of mixture of dextran 1 (D), dextran 5 (T), and poloxamer 188 (P) to chondrocyte treated with RhIL-1α for 24 h As shown in Table 3A and FIG. 5, in the group treated with dextran 1 (D) alone in a single group treatment experiment, increase in the ratio between the expression levels of IL-10 and IL-6 was not identified clearly except for the 50 (w/v) % concentration treated group. However, the significant ratio increase effect was identified in the poloxamer 188 (P) 1 to 20 (w/v) % treated group and in the dextran 5 (T) 2 to 20 (w/v) % group.

As shown in Table 3B and FIG. 5, a significant increase effect of the ratio between expression levels of IL-10 and IL-6 was observed in the mixture of dextran 1 (D) administered group of in a mixture treatment experiment. In the mixture thereof with poloxamer 188 (P) and dextran 5 (T)

rior when administering the mixtures of dextran 1 (D) 5 and 50 (w/v) %, dextran 5 (T) 4 and 40 (w/v) %, and poloxamer 188 (P) 2 and 10 (w/v) %, compared to a case when each of dextran 1 (D) 5 and 50 (w/v) %, dextran 5 (T) 4 and 40 (w/v) %, and poloxamer 188 (P) 2 and 10 (w/v) % was administered alone. Thus, it may be identified that the mixture of dextran 1 (D), dextran 5 (T), and poloxamer 188 (P) has the superiority.

In particular, when administering the mixtures of dextran 1 (D), dextran 5 (T), and poloxamer 188 (P), excellent anti-inflammation effect was achieved in all ranges of dextran 1 (D) 5 and 50 (w/v) %, dextran 5 (T) 4 and 40 (w/v) %, and poloxamer 188 (P) 2 and 10 (w/v) %. All of these mixtures showed anti-inflammation effect. Accordingly, it was identified that the mixtures are effective in the treatment of the inflammatory disease.

Example 4. Identification of Cartilage Substrate Regeneration Effect Based on Changes in MMP-3 and MMP-13 Gene Expression Levels An experiment was conducted to identify the effect of osteoarthritis treatment based on the expression level of the gene of indicator substances for the osteoarthritis evaluation. MMP-3 and MMP-13 are proteins that destroy cartilage substrates. Thus, cartilage protection effect may be evaluated to be excellent when the test substance may effectively inhibit the increase in the gene expression level that may be induced via inflammatory stimulation.

The concentration of dextran 1 was changed to 2.5 to 50 (w/v) %, that of dextran 5 was changed to 2 to 40 (w/v) %, and that of poloxamer 188 was changed to 1 to 20 (w/v) %, and then, the single substance thereof administration or the mixture thereof administration was performed. Accordingly, changes in expression levels of MMP-3 and MMP-13 were identified. Specifically, each test substance was administered to the rat chondrocyte at 1 hour before the rhIL-1α treatment and then the cell was cultured for 24 hours. After removing the supernatant of the cultured cells, the cells were washed with phosphate buffered saline (PBS). RNA was isolated from the washed cells using a GeneAll hybrid-R RNA purification kit (GeneAll, 3033522). Then, the isolated RNA was quantified using nanodrop (Take3 Multi-Volume plate, BioTeK, Instruments, VT, USA), and then diluted to the same concentration for each experimental group. RNA diluted to the same concentration was synthesized to cDNA using PCR (ReverTra AceR qPCR RT Master Mix with gDNA Remover, Toyobo, FSQ-301). Using the synthesized cDNA, gene expression levels of MMP-3 and MMP-13 were identified in a 96 well plate using Real time RT-PCR.

The composition of the primer used in the experiment was shown in the following Table 4. GAPDH as a housekeeping gene was used as a control.

TABLE 4

|  | Forward direction | Reverse direction |
|---|---|---|
| MMP-3 | 5'-TGG GAA GCC AGT GGA AAT G-3' | 5'- CCA TGC AAT GGG TAG GAT GAG-3' |
| MMP-13 | 5' CTG ACC TGG GAT TTC CAA AA -3' | 5' ACA CGT GGT TCC CTG AGA AG 3' |
| GAPDH | 5'- CTC AAC TAC ATG GTC TAC ATG TTC CA -3' | 5'- CTT CCC ATT CTC AGC CTT GAC T -3' |

After mixing the primer, SyBr green (SYBR Premix Ex Taq, Takara, RR420A) and template with each other, Real time RT-PCR was performed via an intercalating method using Real time RT-PCR (CFX 96 touch, Bio rad, Hercules, Calif., USA). The quantitative result (gene expression level) obtained by applying the Ct value to the calibration curve was converted to the value obtained by dividing the gene expression level by the quantitative result of GAPDH as a housekeeping gene.

3.1 Identification of MMP-3 Expression Level Change

Figure 6:
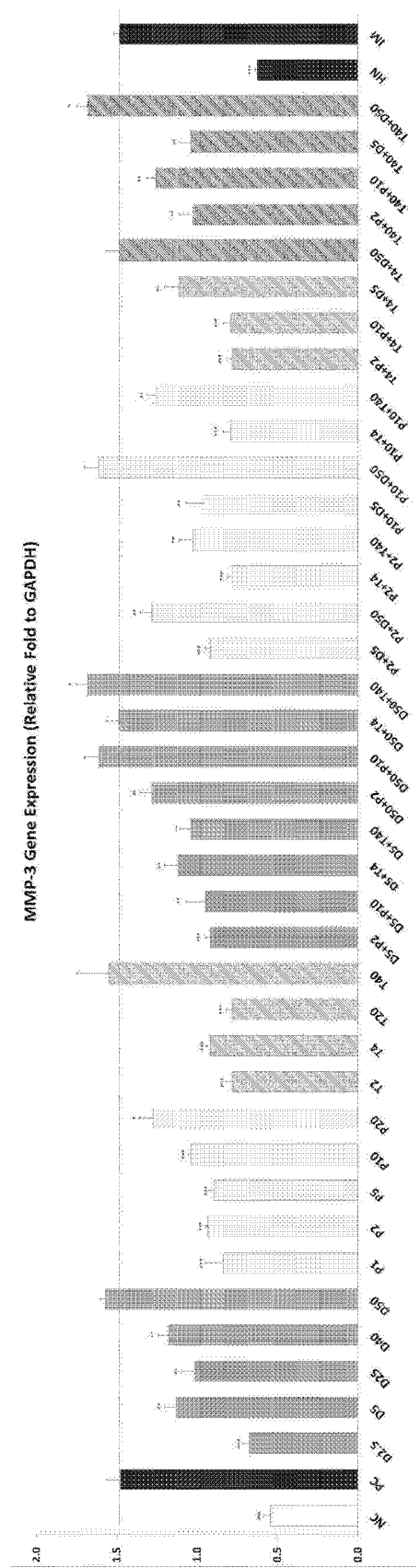
FIG. 6 is a diagram showing results of identifying an expression level of MMP-3 gene when chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

The expression results of MMP-3 due to the administration of dextran 1, dextran 5, poloxamer 188 as a single substance or as a mixture thereof were shown in Table 5A to Table 5B, and FIG. 6.

TABLE 5A

| MMP-3 | NC | PC | D2.5 | D5 | D25 | D40 | D50 | P1 | P2 | P5 | P10 | P20 | T2 | T4 | T20 | T40 | HN | IM |
|---|---|---|---|---|---|---|---|---|---|---|---|---|---|---|---|---|---|---|
| Mean/GAPDH | 0.544 | 1.479 | 0.674 | 1.133 | 1.017 | 1.179 | 1.574 | 0.839 | 0.932 | 0.896 | 1.037 | 1.273 | 0.782 | 0.919 | 0.782 | 1.548 | 0.625 | 1.484 |
| S.D | 0.044 | 0.082 | 0.042 | 0.071 | 0.080 | 0.063 | 0.027 | 0.109 | 0.016 | 0.031 | 0.018 | 0.087 | 0.036 | 0.025 | 0.036 | 0.201 | 0.014 | 0.035 |
| T-test vs. PC | 0.000 |  | 0.000 | 0.003 | 0.001 | 0.004 | 0.065 | 0.001 | 0.000 | 0.000 | 0.000 | 0.020 | 0.000 | 0.000 | 0.000 | 0.304 | 0.000 | 0.462 |

MMP-3 gene expression level due to administration of dextran 1 (D), dextran 5 (T), and poloxamer 188 (P) as a single substance to chondrocyte treated with RhIL-1α for 24 h

TABLE 5B

| MMP-3 | NC | PC | D5 + P2 | D5 + P10 | D5 + T4 | D5 + T40 | D50 + P2 | D50 + P10 | D50 + T4 | D50 + T40 | P2 + D5 | P2 + D50 | P2 + T4 | P2 + T40 | P10 + D5 |
|---|---|---|---|---|---|---|---|---|---|---|---|---|---|---|---|
| Mean/GAPDH | 0.544 | 1.479 | 0.918 | 0.949 | 1.116 | 1.042 | 1.282 | 1.613 | 1.487 | 1.682 | 0.918 | 1.282 | 0.784 | 1.025 | 0.949 |
| S.D | 0.044 | 0.082 | 0.028 | 0.120 | 0.090 | 0.067 | 0.071 | 0.086 | 0.078 | 0.066 | 0.028 | 0.071 | 0.026 | 0.087 | 0.120 |
| T-test vs. PC | 0.000 |  | 0.000 | 0.002 | 0.003 | 0.001 | 0.018 | 0.062 | 0.452 | 0.015 | 0.000 | 0.018 | 0.000 | 0.001 | 0.002 |

TABLE 5B-continued

| MMP-3 | P10 + D50 | P10 + T4 | P10 + T40 | T4 + P2 | T4 + P10 | T4 + D5 | T4 + D50 | T40 + P2 | T40 + P10 | T40 + D5 | T40 + D50 | HN | IM |
|---|---|---|---|---|---|---|---|---|---|---|---|---|---|
| Mean/GAPDH | 1.613 | 0.788 | 1.256 | 0.784 | 0.788 | 1.116 | 1.487 | 1.025 | 1.256 | 1.042 | 1.082 | 0.625 | 1.484 |
| S.D | 0.086 | 0.050 | 0.056 | 0.026 | 0.050 | 0.090 | 0.078 | 0.087 | 0.056 | 0.067 | 0.066 | 0.014 | 0.035 |
| T-test vs. PC | 0.062 | 0.000 | 0.009 | 0.000 | 0.000 | 0.003 | 0.452 | 0.001 | 0.009 | 0.001 | 0.015 | 0.000 | 0.462 |

MMP-3 gene expression level due to administration of dextran 1 (D), dextran 5 (T) and poloxamer 188 (P) as a mixture thereof to chondrocyte treated with RhIL-1α for 24 h As shown in Table 5A and FIG. 6, dextran 1 (D) at 2.5 to 40 (w/v) % exerted a significant MMP-3 expression level decrease effect compared to the inflammation-induced positive control. The dextran 5 (T) showed significant MMP-3 expression level decrease effect at 2 to 20 (w/v) %. Meanwhile, poloxamer 188 (P) showed the MMP-3 expression level decrease effect at 1 to 20 (w/v) % in all test groups.

As shown in Table 5B and FIG. 6, in the mixture experimental group, the mixture of dextran 1 (D) 5 (w/v) % and poloxamer 188 (P) 2 to 10 (w/v) %, dextran (T) 4% and 40 (w/v) % showed significant MMP-3 expression level decrease effect in all experimental groups. In the group treated with the high concentration of dextran 1 (D) up to 50 (w/v) %, a significant decrease effect was identified only when the dextran 1 (D) was mixed with P2. Thus, it was identified that when the mixture of dextran 1 with dextran 5 or poloxamer 188 was used, it is desirable to control the concentration of the dextran 1 (D) to be lower than 50 (w/v) %. Poloxamer 188 showed the significant MMP-3 expression level decrease effect in a single substance treated group and in a mixture treated group. As identified in Example 2, it was identified that the concentration of poloxamer is preferably 10 (w/v) % or smaller, and the corresponding P2, P5, and P10 may induce a significant MMP-3 inhibition effect even in combination with dextran 1 and dextran 5.

3.2 Identification of MMP-13 Expression Level Change

Figure 7:
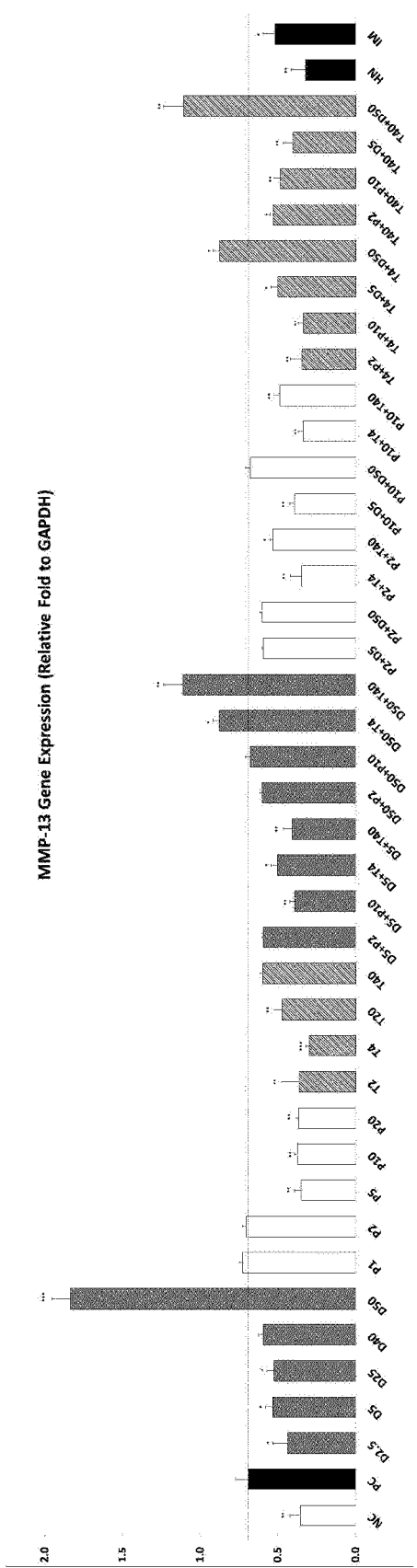
FIG. 7 is a diagram showing results of identifying an expression level of MMP-13 gene when chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

The expression level results of MMP-13 due to administration of dextran 1, dextran 5, and poloxamer 188 as a single substance or as a mixture thereof were shown in Tables 6A to 6B, and FIG. 7.

TABLE 6A

| MMP-13 | NC | PC | D2.5 | D5 | D25 | D40 | D50 | P1 | P2 | P5 | P10 | P20 | T2 | T4 | T20 | T40 | HN | IM |
|---|---|---|---|---|---|---|---|---|---|---|---|---|---|---|---|---|---|---|
| Mean/GAPDH | 0.352 | 0.687 | 0.435 | 0.534 | 0.521 | 0.593 | 1.834 | 0.725 | 0.703 | 0.347 | 0.370 | 0.362 | 0.363 | 0.297 | 0.470 | 0.599 | 0.321 | 0.513 |
| S.D | 0.069 | 0.083 | 0.097 | 0.042 | 0.047 | 0.026 | 0.116 | 0.017 | 0.023 | 0.047 | 0.023 | 0.023 | 0.113 | 0.021 | 0.054 | 0.010 | 0.094 | 0.077 |
| T-test vs. PC | 0.003 | | 0.014 | 0.023 | 0.020 | 0.069 | 0.000 | 0.243 | 0.380 | 0.002 | 0.002 | 0.001 | 0.008 | 0.001 | 0.010 | 0.072 | 0.004 | 0.029 |

MMP-13 gene expression level due to administration of dextran 1 (D), dextran 5 (T), and poloxamer 188 (P) as single substance to chondrocyte treated with RhIL-1α for 24 h

TABLE 6B

| MMP-13 | NC | PC | D5 + P2 | D5 + P10 | D5 + T4 | D5 + T40 | D50 + P2 | D50 + P10 | D50 + T4 | D50 + T40 | P2 + D5 | P2 + D50 | P2 + T4 | P2 + T40 | P10 + D5 |
|---|---|---|---|---|---|---|---|---|---|---|---|---|---|---|---|
| Mean/GAPDH | 0.352 | 0.687 | 0.593 | 0.390 | 0.499 | 0.406 | 0.599 | 0.676 | 0.874 | 1.108 | 0.593 | 0.599 | 0.344 | 0.533 | 0.390 |
| S.D | 0.069 | 0.083 | 0.007 | 0.032 | 0.044 | 0.055 | 0.014 | 0.028 | 0.039 | 0.126 | 0.007 | 0.014 | 0.075 | 0.016 | 0.032 |
| T-test vs. PC | 0.003 | | 0.062 | 0.002 | 0.013 | 0.004 | 0.073 | 0.424 | 0.012 | 0.004 | 0.062 | 0.073 | 0.003 | 0.017 | 0.002 |

| MMP-13 | P10 + D50 | P10 + T4 | P10 + T40 | T4 + P2 | T4 + P10 | T4 + D5 | T4 + D50 | T40 + P2 | T40 + P10 | T40 + D5 | T40 + D50 | HN | IM |
|---|---|---|---|---|---|---|---|---|---|---|---|---|---|
| Mean/GAPDH | 0.676 | 0.334 | 0.483 | 0.344 | 0.334 | 0.499 | 0.874 | 0.533 | 0.483 | 0.406 | 1.108 | 0.321 | 0.513 |
| S.D | 0.028 | 0.031 | 0.041 | 0.075 | 0.031 | 0.044 | 0.039 | 0.016 | 0.041 | 0.055 | 0.126 | 0.094 | 0.077 |
| T-test vs. PC | 0.424 | 0.001 | 0.010 | 0.003 | 0.001 | 0.013 | 0.012 | 0.017 | 0.010 | 0.004 | 0.004 | 0.004 | 0.029 |

MMP-13 gene expression level due to administration of dextran 1 (D), dextran 5 (T) and poloxamer 188 (P) as mixture thereof to chondrocyte treated with RhIL-1α for 24 h As may be seen from the Table 6A to Table 6B, FIG. 7, dextran 1 (D) in the single substance experiment group exhibited a significant inhibition effect of MMP-13 gene expression level increase at 2.5 to 25 (w/v) %. D40 at 40 (w/v) % did not exhibit the significant inhibition effect of the MMP-13 gene expression level increase but exhibited mere MMP-13 gene expression level increase inhibition. D50 at 50 (w/v) % exhibited the MMP-13 gene expression level increase. These properties occurred in a similar manner in the mixture of dextran 1 (D). Thus, it was identified that the most desirable concentration range of the dextran 1 (D) is 2.5 to 40 (w/v) %. This was consistent with the MMP-3 gene expression level result. The dextran 5 (T) showed the significant MMP-13 gene expression level increase inhibition effect at 2 to 40 (w/v) % in the single substance administration. The dextran 5 (T) 4 and 40 (w/v) % exhibited the significant MMP-13 gene expression level increase inhibition effect even when being mixed with dextran 1 (D) 5 (w/v) % and poloxamer 188 (P) 2 and 10 (w/v) %.

In the single substance experimental group, poloxamer 188 at 5 to 20 (w/v) % showed the MMP-13 gene expression level increase inhibition effect. However, the mixture of the poloxamer 188 with dextran was used, poloxamer 188 2 (w/v) % showed the MMP-13 gene expression level increase inhibition effect. It was identified that considering the results of the cytotoxicity experiment in Example 2, the concentration of poloxamer 188 (P) was preferably 2 to 10 (w/v) % when the mixture thereof was administered. The corresponding P2 and P10 induces the significant MMP-13 gene expression level increase inhibition effect in combination with dextran 1 and dextran 5, except for the combination thereof with dextran 1 (D) 50 (w/v) %.

Based on the above results, it was identified that P2, P5, and P10 may induce the significant MMP-13 inhibition effect even in combination with dextran 1 and dextran 5.

Example 5. Identification of Production Level Increase of Type II Collagen and Aggrecan in Osteoarthritis Induced Model In order to identify protein production levels of the type II collagen and aggrecan among indicator substances for osteoarthritis evaluation, each test substance was administered to chondrocytes at 1 hour before the treatment with rhIL-1α, and then the cell was cultured for 24 hours. Type II collagen and aggrecan are cartilage substrate compositions. Thus, when the production levels thereof are increased, the cartilage substrate protection effect may be excellent.

In this connection, cell supernatant (culture solution) was collected and centrifuged at 13,000 rpm for 10 minutes, and thus only the supernatant was used for analysis. The centrifuged cell supernatant was analyzed using Aggrecan ELISA Kit (Rat Aggrecan ELISA Kit, Mybiosource, MBS261073) and with reference to the manuals of the type II Collagen (Type II Collagen detection Kit, Multi-Species, Chondrex, 6018). For accurate analysis, absorbance was measured at 450 nm and 490 nm using an ELISA reader (EPOCH 2 microplate reader, BioTek, Instruments, VT, USA) of the entire wavelength range. The contents (ng/mL) of the type II collagen and aggrecan were quantified according to the calibration curve.

5.1 Identification of Type II Collagen Production Level

Figure 8:
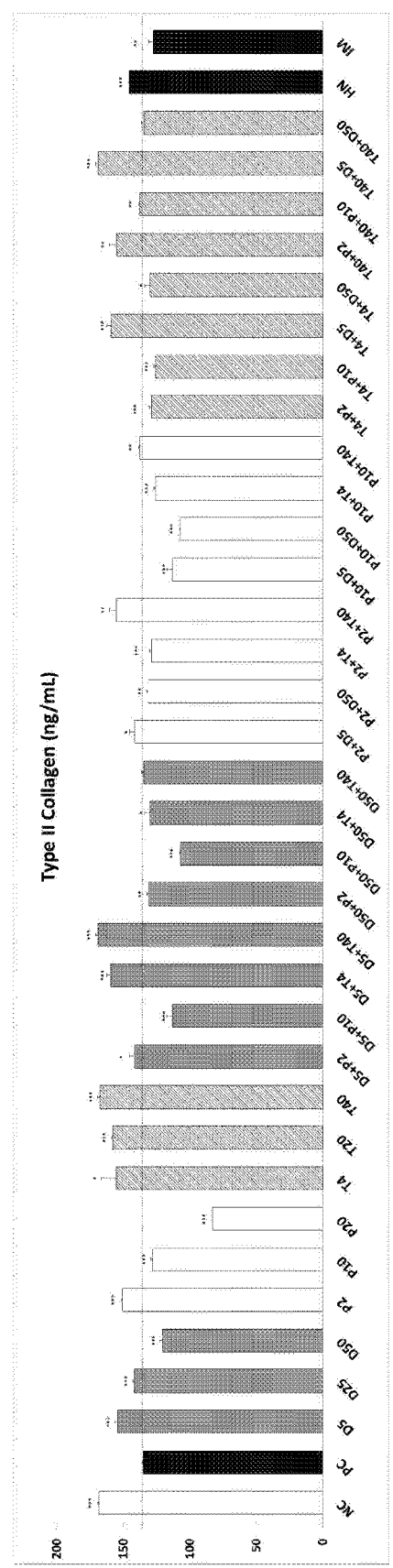
FIG. 8 is a diagram showing results of identifying a production level of a type II collagen when chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

The production level results of the type II collagen due to administration of dextran 1 (D), dextran 5 (T), and poloxamer 188 (P) as a single substance or as a mixture thereof were shown in Table 7A to Table 7B, and FIG. 8.

TABLE 7A

| Type II Collagen | NC | PC | D5 | D25 | D50 | P2 | P10 | P20 | T4 | T20 | T40 | HN | IM |
|---|---|---|---|---|---|---|---|---|---|---|---|---|---|
| Mean (ng/mL) | 168.3 | 135.2 | 154.4 | 141.5 | 120.5 | 151.0 | 127.9 | 82.6 | 155.4 | 157.9 | 167.6 | 145.4 | 127.3 |
| S.D | 0.9 | 0.5 | 1.7 | 1.1 | 2.4 | 0.4 | 11 | 0.1 | 11.3 | 0.6 | 1.8 | 13 | 3.2 |
| T-test vs. PC | 0.000 | | 0.000 | 0.000 | 0.000 | 0.000 | 0.000 | 0.000 | 0.018 | 0.000 | 0.000 | 0.000 | 0.007 |

Type II Collagen production level due to administration of dextran 1 (D), dextran 5 (T), poloxamer 188 (P) as single substance to chondrocyte treated with RhIL-1α for 24 h

TABLE 7B

| Type II Collagen | NC | PC | D5 + P2 | D5 + P10 | D5 + T4 | D5 + T40 | D50 + P2 | D50 + P10 |
|---|---|---|---|---|---|---|---|---|
| Mean (ng/mL) | 168.3 | 135.2 | 141.2 | 112.9 | 159.2 | 169.0 | 131.0 | 107.0 |
| S.D | 0.9 | 0.5 | 3.9 | 4.7 | 2.9 | 1.7 | 1.5 | 0.6 |
| T-test vs. PC | 0.000 | | 0.027 | 0.001 | 0.000 | 0.000 | 0.005 | 0.000 |

| Type II Collagen | D50 + T4 | D50 + T40 | P2 + D5 | P2 + D50 | P2 + T4 | P2 + T40 | P10 + D5 | P10 + D50 |
|---|---|---|---|---|---|---|---|---|
| Mean (ng/mL) | 129.9 | 134.8 | 141.2 | 131.0 | 128.7 | 155.2 | 112.9 | 107.0 |
| S.D | 4.2 | 1.3 | 3.9 | 1.5 | 1.2 | 5.2 | 4.7 | 0.6 |

TABLE 7B-continued

| T-test vs. PC | 0.047 | 0.345 | 0.027 | 0.005 | 0.000 | 0.001 | 0.001 | 0.000 |

| Type II Collagen | P10 + T4 | P10 + T40 | T4 + P2 | T4_P10 | T4 + D5 | T4 + D50 | T40 + P2 |
|---|---|---|---|---|---|---|---|
| Mean (ng/mL) | 125.8 | 137.6 | 128.7 | 125.8 | 159.2 | 129.9 | 155.2 |
| S.D | 0.8 | 0.8 | 1.2 | 0.8 | 2.9 | 4.2 | 5.2 |
| T-test vs. PC | 0.000 | 0.005 | 0.000 | 0.000 | 0.000 | 0.047 | 0.001 |

| Type II Collagen | T40 + P10 | T40 + D5 | T40 + D50 | HN | IM |
|---|---|---|---|---|---|
| Mean (ng/mL) | 137.6 | 169.0 | 134.8 | 145.4 | 127.3 |
| S.D | 0.8 | 1.7 | 1.3 | 1.3 | 3.2 |
| T-test vs. PC | 0.005 | 0.000 | 0.345 | 0.000 | 0.007 |

Type II Collagen production level due to administration of dextran 1 (D), dextran 5 (T) or poloxamer 188 (P) as mixture thereof to chondrocyte treated with RhIL-1α for 24 h As shown in the Table 7A to Table 7B, and FIG. 8, in the dextran 1 (D) 5 to 25 (w/v) %, and dextran 5 (T) 4 to 40 (w/v) % single substance administered groups, the increase in the type II collagen synthesis compared to the inflammation-induced positive control (PC) was observed. Meanwhile, the dextran 1 (D) 50 (w/v) % did not induce an increase in the type II collagen synthesis compared to the inflammation-induced positive control (PC) both in single substance administered groups and in a mixture thereof with dextran 5 (T) and poloxamer 188 (P) administered group. Thus, considering that the dextran 1 (D) 50 (w/v) % alone does not show the effect of inhibiting the increase in the expression level of MMP-3 and MMP-13 but the dextran 1 (D) 50 (w/v) % shows the effect of inhibiting the increase in the expression level of MMP-3 and MMP-13 only when being mixed with poloxamer 188 (P) 2 to 10 (w/v) %, as identified in Example 4, it may be preferable that the dextran 1 (D) may have the concentration equal to or lower than 40 (w/v) % in a single substance administration mode or in a mixture administration mode. In particular, when the mixture between the dextran 1 (D) 5 (w/v) % and dextran 5 (T) 4 to 40 (w/v) % was used, the type II collagen synthesis was significantly increased compared to inflammation-induced positive control (PC).

The poloxamer 188 (P) did not show the type II collagen synthesis increase effect in the 10 (w/v) % and 20 (w/v) % single substance treated groups, except the 2 (w/v) % single substance treated group. As the type II collagen synthesis further decreased as the concentration thereof increased. However, when the poloxamer 188 (P) 2 or 10 (w/v) % was mixed with dextran 1 (D) 5 (w/v) % or dextran 5 (T) 40 (w/v) %, the type II collagen synthesis increase effect was significant. These results show that each of the dextran 1 (D) and dextran 5 (T) may be administered alone for the type II collagen synthesis of the osteoarthritis, but the poloxamer 188 (P) alone is not suitable for the type II collagen synthesis of the osteoarthritis, except for 2 (w/v) %. The administration of a mixture of poloxamer 188 (P) and dextran 1 (D) or dextran 5 (T) may effectively induce the type II collagen synthesis.

It was identified based on the above Example 3, that the administration of the mixture of poloxamer 188 and dextran 1 or dextran 5 may significantly increase the ratio between the gene expression levels of IL-10 and IL-6, compared to the single substance administration. Thus, based on the combined results, it was identified that it is desirable to administer a mixture of dextran 1, dextran 5 or poloxamer 188 in order to alleviate the inflammatory response in osteoarthritis and promote the collagen synthesis.

5.2 Identification of Aggrecan Content Quantitative Results

Figure 9:
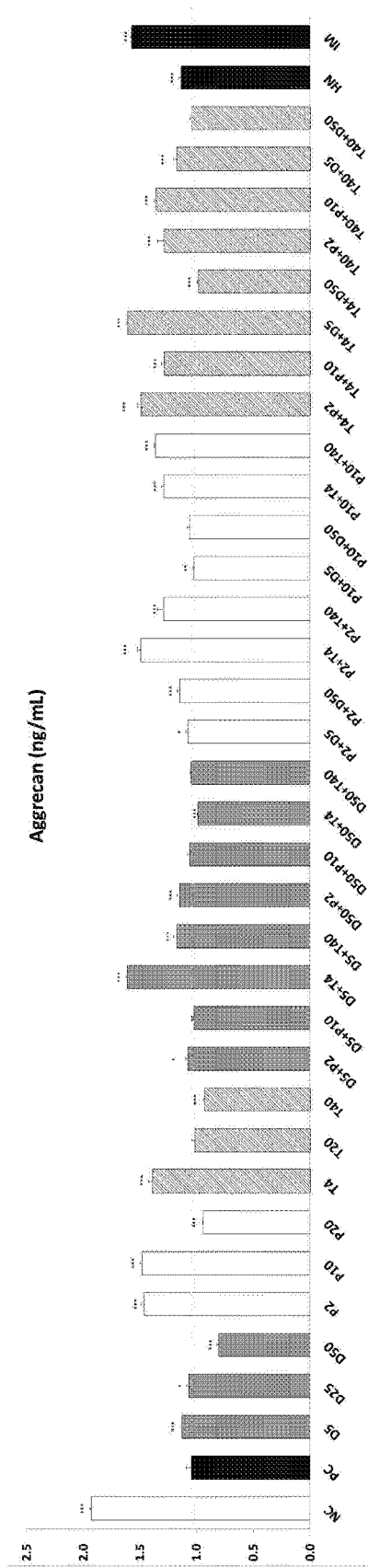
FIG. 9 is a diagram showing results of identifying a production level of aggrecan when chondrocyte of an osteoarthritis in vitro model caused by rhIL-1α treatment is treated with dextran, poloxamer, or a mixture treatment (*//* represent significance levels of $p<0.05$/$p<0.01$/$p<0.001$ respectively, compared to inflammation-induced positive control (pc)).

Results of the aggrecan production level due to administration of dextran 1, dextran 5, and poloxamer 188 as a single substance or a mixture thereof were shown in Table 8A to Table 8B, and FIG. 9.

TABLE 8A

| Aggrecan | NC | PC | D5 | D25 | D50 | P2 | P10 | P20 | T4 | T20 | T40 | HN | IM |
|---|---|---|---|---|---|---|---|---|---|---|---|---|---|
| Mean (ng/mL) | 1.933 | 1.047 | 1.129 | 1.072 | 0.803 | 1.463 | 1.483 | 0.943 | 1.394 | 1.014 | 0.933 | 1.137 | 1.573 |
| S.D | 0.010 | 0.048 | 0.016 | 0.020 | 0.013 | 0.029 | 0.019 | 0.004 | 0.030 | 0.027 | 0.007 | 0.020 | 0.010 |
| T-test vs. PC | 0.000 | | 0.000 | 0.045 | 0.000 | 0.000 | 0.000 | 0.000 | 0.000 | 0.054 | 0.000 | 0.001 | 0.000 |

Aggrecan production level due to administration of dextran 1 (D), dextran 5 (T) or poloxamer 188 (P) as single substance to chondrocyte treated with RhIL-1α for 24 h

TABLE 8B

| Aggrecan | NC | PC | D5 + P2 | D5 + P10 | D5 + T4 | D5 + T40 | D50 + P2 | D50 + P10 | D50 + T4 | D50 + T40 | P2 + D5 | P2 + D50 | P2 + T4 | P2 + T40 | P10 + D5 |
|---|---|---|---|---|---|---|---|---|---|---|---|---|---|---|---|
| Mean (ng/mL) | 1.933 | 1.047 | 1.079 | 1.021 | 1.610 | 1.176 | 1.150 | 1.066 | 0.986 | 1.051 | 1.079 | 1.150 | 1.496 | 1.294 | 1.021 |

TABLE 8B-continued

| | | | | | | | | | | | | | | | |
|---|---|---|---|---|---|---|---|---|---|---|---|---|---|---|---|
| S.D | 0.010 | 0.048 | 0.016 | 0.010 | 0.010 | 0.027 | 0.023 | 0.016 | 0.006 | 0.006 | 0.016 | 0.023 | 0.028 | 0.052 | 0.010 |
| Test vs. PC | 0.000 | | 0.014 | 0.007 | 0.000 | 0.001 | 0.001 | 0.057 | 0.000 | 0.187 | 0.014 | 0.001 | 0.000 | 0.001 | 0.007 |

| Aggrecan | P10 + D50 | P10 + T4 | P10 + T40 | T4 + P2 | T4 + P10 | T4 + D5 | T4 + D50 | T40 + P2 | T40 + P10 | T40 + D5 | T40 + D50 | HN | IM |
|---|---|---|---|---|---|---|---|---|---|---|---|---|---|
| Mean (ng/mL) | 1.066 | 1.290 | 1.361 | 1.496 | 1.290 | 1.610 | 0.986 | 1.294 | 1.361 | 1.176 | 1.051 | 1.137 | 1.573 |
| S.D | 0.016 | 0.023 | 0.013 | 0.028 | 0.023 | 0.010 | 0.006 | 0.052 | 0.013 | 0.027 | 0.006 | 0.020 | 0.010 |
| Test vs. PC | 0.057 | 0.000 | 0.000 | 0.000 | 0.000 | 0.000 | 0.000 | 0.001 | 0.000 | 0.001 | 0.187 | 0.001 | 0.000 |

Aggrecan production level due to administration of dextran 1 (D), dextran 5 (T) and poloxamer 188 (P) as mixture thereof to chondrocyte treated with RhIL-1α for 24 h As may be seen in Table 6A and FIG. 9, it was identified that each of dextran 1 (D) 5 to 25 (w/v) %, dextran 5 (T) 4 (w/v) %, poloxamer 188 (P) 2 to 10 (w/v) % in a single substance treated group significantly increased the aggrecan production level compared to the inflammation-induced positive control (PC). Meanwhile, each of the dextran 1 (D) 50 (w/v) %, poloxamer 188 (P) 20 (w/v) %, and dextran 5 (T) 20 to 40 (w/v) % in a single substance administered group failed to induce the aggrecan production level increase.

As may be seen in Table 8B and FIG. 9, the mixture between dextran 1 (D) 5 (w/v) % and poloxamer 188 (P) 2 (w/v) % or dextran 5 (T) 4 to 40 (w/v) % in the mixture administered groups significantly increased the aggrecan production level compared to the inflammation-induced positive control (PC). The aggrecan production level was significantly increased only in the group administered with a mixture of dextran 1 (D) 50 (w/v) % and poloxamer 188 (P) 2 (w/v) %. The aggrecan production level was also significantly increased in the mixture between dextran 5 (T) 4 to 40 (w/v) % and poloxamer 188 (P) 2 to 10 (w/v) % administered group, compared to the inflammation-induced positive control (PC). In particular, the dextran 1 (D) 5 (w/v) % and poloxamer 188 (P) 2 (w/v) % significantly increased the aggrecan production level in a mixture administration mode with dextran 5 (T) 4 to 40 (w/v) %, compared to the single administration mode.

Considering the results of the type II collagen synthesis identified in Example 5.1 as described above, dextran 1 (D) 5 to 25 (w/v) %, dextran 5 (T) 4 (w/v) %, or poloxamer 188 (P) 2 (w/v) % may be used in a single substance administration mode in order to increase the type II collagen synthesis and to increase the aggrecan production in the osteoarthritis model. Further, dextran 1 (D) 5 (w/v) % may be combined with dextran 5 (T) 4 to 40 (w/v) %, or dextran 1 (D) 5 (w/v) % may be combined with poloxamer 188 (P) 2 (w/v) % in order to increase the type II collagen synthesis and to increase the aggrecan production in the osteoarthritis model. Further, it was identified that when dextran 5 (T) 4 to 40 (w/v) % is in combination with dextran 1 (D) 5 (w/v) %, especially, when dextran 5 40 (w/v) % is in combination with poloxamer 188 (P) 2 to 10 (w/v) %, the type II collagen synthesis and the aggrecan production could be significantly increased.

Based on synthesizing of the above results, it may be identified that dextran 1, dextran 5 and poloxamer 188 may be used in the treatment of osteoarthritis, but dextran 1, dextran 5 and poloxamer 188 alone or all combinations thereof do not always show the therapeutic effect on osteoarthritis, but the toxicity and the effect may vary based on the concentrations of dextran 1, dextran 5, and poloxamer 188. Thus, it is important to derive an appropriate combination thereof based on the above findings.

The invention claimed is:

1. A method of regenerating or protecting of a cartilage, the method comprising administering to a subject in need thereof a composition comprising dextran having an average molecular weight in a range of 3,000 Da to 8,000 Da.

2. The method of claim 1, wherein a concentration of dextran in the composition is in a range of 2 to 40 (w/v) %.

3. The method of claim 1, the composition further comprising dextran having an average molecular weight in a range of 800 Da to 1,200 Da.

4. The method of claim 3,
wherein a concentration of the dextran having an average molecular weight in a range of 3,000 Da to 8,000 Da is in a range of 2 to 40 (w/v) % in the composition, and a concentration of the dextran having an average molecular weight in a range of 800 Da to 1,200 Da is in a range of 2.5 to 40 (w/v) % in the composition.

5. The method of claim 3, wherein a ratio between concentrations (w/v) % of dextran having an average molecular weight in a range of 800 Da to 1,200 Da, and dextran having an average molecular weight in a range of 3,000 Da to 8,000 Da in the composition is in a range of 1:0.01 to 1:20.

6. The method of claim 1, the composition further comprising poloxamer.

7. The method of claim 6, wherein a concentration of the dextran in the composition is in a range of 2 to 40 (w/v) % and a concentration of the poloxamer is in a range of 1 to 20 (w/v) %.

8. The method of claim 6, wherein a ratio between concentrations (w/v) % of dextran and poloxamer in the composition is in a range of 1:0.01 to 1:40.

9. The method of claim 1, wherein the dextran has an average molecular weight in a range of 4,000 Da to 6,000 Da.

10. The method of claim 1, wherein the dextran has an average molecular weight in a range of 4,500 Da to 5,500 Da.

11. The method of claim 1, wherein the method further inhibits inflammation of joints, cartilages, or connective tissues.

12. The method of claim 1, the composition further comprising a stem cell.

* * * * *